United States Patent
Buck et al.

(10) Patent No.: US 7,217,565 B2
(45) Date of Patent: *May 15, 2007

(54) ENRICHED CENTRAL NERVOUS SYSTEM STEM CELL AND PROGENITOR CELL POPULATIONS, AND METHODS FOR IDENTIFYING, ISOLATING AND ENRICHING FOR SUCH POPULATIONS

(75) Inventors: David W. Buck, Eugene, OR (US); Nobuko Uchida, Palo Alto, CA (US); Irving Weissman, Redwood City, CA (US)

(73) Assignee: StemCells California, Inc., Palo Alto, CA (US)

( * ) Notice: Subject to any disclaimer, the term of this patent is extended or adjusted under 35 U.S.C. 154(b) by 740 days.

This patent is subject to a terminal disclaimer.

(21) Appl. No.: 10/193,049

(22) Filed: Jul. 11, 2002

(65) Prior Publication Data

US 2003/0109039 A1    Jun. 12, 2003

Related U.S. Application Data

(63) Continuation-in-part of application No. 09/422,844, filed on Oct. 21, 1999, now Pat. No. 6,468,794.

(60) Provisional application No. 60/339,337, filed on Nov. 5, 2001, provisional application No. 60/119,725, filed on Feb. 12, 1999.

(51) Int. Cl.
    *C12N 5/08*    (2006.01)

(52) U.S. Cl. ..................................... 435/368; 435/343

(58) Field of Classification Search ................ 435/332, 435/368, 343, 335; 424/93.7, 140.1, 153.1
See application file for complete search history.

(56) References Cited

U.S. PATENT DOCUMENTS 5,750,376 A    5/1998    Weiss et al.
5,753,506 A    5/1998    Johe
5,843,633 A    12/1998   Yin et al.
5,851,832 A    12/1998   Weiss et al.
5,968,829 A    10/1999   Carpenter

FOREIGN PATENT DOCUMENTS

WO    WO 94/02593    2/1994
WO    WO 00/12683    3/2000

OTHER PUBLICATIONS

Corbeil et al., *AC133 Hematopoietic Stem Cell Antigen: Human Homologue of Mouse Kidney Prominin or Distinct Member of a Novel Protein Family?* 91 BLOOD 2625 (1998).
De Wynter et al., *Characteristics of MACS Isolated CD34+AC133+ Hematopoietic Progenitor Cells*, 2 MACS & MORE 8 (1998).
Miraglia et al., *AC133, A New Antigen for Human Hematopoietic Stem Cells. Is Prominin the Murine Homologue?* 2 MACS & MORE 6 (1998).
Miraglia et al., *A Novel Five-Transmembrane Hematopoietic Stem Cell Antigen: Isolation, Characterization, and Molecular Cloning*, 90 BLOOD 5013 (1997).
Miraglia et al., *A Response to AC133 Hematopoietic Stem Cell Antigen: Human Homologue of Mouse Kidney Prominin or Distinct Member of a Novel Protein Family?* 91 BLOOD 4390 (1998).
Yin et al., *AC133, A Novel Marker for Human Hematopoietic Stem and Progenitor Cells*, 90 BLOOD 5002 (1997).
Uchida et al. Society for Neuroscience Abstracts 25 (1-2): 1767 (1999).
Corbein et al., Journal of Cell Science, 112:1023-1033 (1999).
CD133 Cell Isolation Kit, MACS, (Miltenyi Biotec, Auburn, CA) (downloaded Dec. 11, 2001).
Weigmarin et al. Proc. Natl. Acad. Sci. USA, 94(23):12425-12430 (1997).
Arsenijevic et al., "Isolation of Multipotent Neural Precursors Residing in the Cortex of the Adult HUman Brain", *Exp. Neural.*, 170:48-62 (2001).

*Primary Examiner*—Robert C. Hayes
(74) *Attorney, Agent, or Firm*—Mintz, Levin, Cohn, Ferris, Glovksy and Popeo, P.C.; Ivor R. Elriffi; Christina K. Stock

(57) ABSTRACT

Enriched neural stem and progenitor cell populations, and methods for identifying, isolating and enriching for neural stem cells using reagent that bind to cell surface markers, are provided.

23 Claims, 8 Drawing Sheets

ENRICHED CENTRAL NERVOUS SYSTEM STEM CELL AND PROGENITOR CELL POPULATIONS, AND METHODS FOR IDENTIFYING, ISOLATING AND ENRICHING FOR SUCH POPULATIONS

CLAIM OF PRIORITY

This application claims the benefit of U.S. Ser. No. 60/339,337, filed Nov. 5, 2001, and is a continuation-in-part of U.S. Ser. No. 09/422,844, filed Oct. 21, 1999, now U.S. Pat. No. 6,468,794 which claims priority to U.S. Ser. No. 60/119,725, filed Feb. 12, 1999, each of which is incorporated herein by reference.

TECHNICAL FIELD

This invention relates generally to enriched neural stem cell and progenitor cell populations, and methods for identifying, isolating and enriching for neural stem and progenitor cells, particularly central nervous system neural stem cells and progenitor cells, and most particularly to enriched populations of neurosphere initiating cells (NS-IC).

BACKGROUND OF THE INVENTION

Stem cell populations constitute only a small percentage of the total number of cells, but are of immense interest because of their ability to repopulate the body. The longevity of stem cells and the dissemination of stem cell progeny are desirable characteristics. There is significant commercial interest in these methods because stem cells have a number of clinical uses. There is also medical interest in the use of stem cells as a vehicle for gene therapy.

Proteins and other cell surface markers found on stem cell and progenitor cell populations are useful in preparing reagents for the separation and isolation of these populations. Cell surface markers are also useful in the further characterization of these important cells.

Yin et al., U.S. Pat. No. 5,843,633, incorporated herein by reference, describes a monoclonal antibody called AC133, which binds to a surface marker glycoprotein on hematopoietic stem and progenitor cells. The AC133 antigen is a 5-transmembrane cell surface antigen with a molecular weight of 117 kDa. Expression of this antigen is highly tissue specific, and has been detected on a subset of hematopoietic progenitor cells derived from human bone marrow, fetal bone marrow and liver, cord blood, and adult peripheral blood. The subset of cells recognized by the AC133 antibody is $CD34^{bright}$, and contains substantially all of the CFU-GM activity present in the $CD34^+$ population, making AC133 useful as a reagent for isolating and characterizing human hematopoietic progenitor and stem cells.

However, surface markers specific to non-hematopoietic stem cells and progenitor cells, and particularly central nervous system neural stem cells and progenitor cells have not been identified. Further, the AC133 antibody has not been used in methods for identifying, isolating, or enriching for non-hematopoietic stem cells or progenitor cells, particularly central nervous system (CNS) neural stem cells and progenitor cells. There remains a need for tools, such as monoclonal antibodies that are useful in isolating and characterizing human non-hematopoietic progenitor and stem cells, and particularly central nervous system (CNS) neural stem cells and progenitor cells.

SUMMARY OF THE INVENTION

This invention provides methods for identifying, isolating, and enriching for human non-hematopoietic progenitor and stem cells, and particularly central nervous system (CNS) neural stem cells which can initiate neurospheres (NS-IC) and progenitor cells. The invention also provides for enriched populations containing CNS neural stem cells that can initiate neurospheres, and progenitor cells. A "neurosphere initiating cell (NS-IC)" is a cell that can initiate long-term neurosphere culture. A "neurosphere", in turn, is an aggregate or cluster of cells which includes neural stem cells and primitive progenitors. The identification, culture, growth, and use of neurospheres is disclosed in Weiss et al., U.S. Pat. No. 5,750,376 and Weiss et al., U.S. Pat. No. 5,851,832, both incorporated herein by reference. While the term "NS-IC" is defined by the ability or capacity of that cell to form a neurosphere, these cells may be appropriately grown in adherent culture (see, for example, Johe, U.S. Pat. No. 5,753,506, incorporated herein by reference), and it should be noted that the methods and populations described herein are not to be limited to suspension cultures of NS-IC. An NS-IC is $nestin^+$ and has the capability to differentiate, under appropriate differentiating conditions, to neurons, astrocytes, and oligodendrocytes.

According to one aspect of this invention, enriched populations of non-hematopoietic stem cells and progenitor cells, preferably CNS neural stem cells including NS-ICs, and progenitor cells, and a method of identifying, isolating, or enriching for such cells, is achieved by contacting a population of cells containing at least one stem cell or NS-IC, or progenitor cell with a reagent that binds to surface marker glycoprotein antigen ("AC133 antigen") recognized by the AC133 antibody. As used herein, the term "reagent" is meant to include any composition or compound that is capable of binding to, associating with, or recognizing an antigen. Examples of such reagents include, but are not limited to monoclonal antibodies, polyclonal antibodies, small molecules, receptors, ligands, proteins, protein fragments, polypeptides, polypeptide fragments, nucleic acids, nucleic acid fragments, antibody fragments, and any other "reagents" known to those skilled in the art.

In a preferred embodiment the reagent is the AC133 antibody (the AC133 antibody is alternately referred to herein as "5F3"). Use of traditional techniques for cell sorting, such as by immunoselection (e.g., FACS), then permits identification, isolation, and/or enrichment for cells in which contact between the reagent and the AC133 antigen has been detected.

In another aspect, this invention provides a novel antibody, herein called 5E12, that may be used to provide enriched populations of non-hematopoietic stem cells and progenitor cells, preferably CNS neural stem cells that can initiate neurospheres and progenitor cells, and may be used in methods of identifying, isolating, or enriching for such cells, by contacting a population of cells containing at least one stem cell NS-IC, or progenitor cell with the 5E12 antibody, which binds to a surface marker glycoprotein antigen other than the AC133 antigen.

In a preferred aspect, the cells of this invention, preferably the CNS neural stem cells, are additionally characterized as lacking cell surface markers for CD45 and CD34.

In a further aspect, this invention provides a novel antibody, herein called 8G1, believed to recognize CD24, which permits subselection between populations of CNS neural stem cells (characterized as $8G1^{-/lo}$) and populations of CNS progenitor cells (characterized as $8G1^+$). Other antibodies that recognize CD24 include 32D12 (Diatec (Oslo, NORWAY)); ALB9 (Accurate Chemical and Scientific Co. (Westbury, N.Y.); BEK (Miami, Fla.); Biomeda Corporation, (Foster City, Calif.); Biosource International (Camarillo, Calif.); Leinco Technologies (St. Louis, Mo.); Research Diagnostics, Inc. (Flanders, N.J.)); CLB134 (Accurate Chemical and Scientific Co. (Westbury, N.Y.); Cell Sciences (Norwood, Mass.)); CLBGRANBLy1 (Accurate Chemical and Scientific Co. (Westbury, N.Y.); Research Diagnostics, Inc. (Flanders, N.J.)); SN3 (Caltac Laboratories, Inc. (Burlingame, Calif.)); ML5 (BD Pharmingen (San Diego, Calif.)); and 24C02 (Lab Vision Corporation (Freemont, Calif.); United States Biological (Swampscott, Mass.)).

In a further aspect, the invention involves a method for producing a population enriched for human CNS-SC which can initiate neurospheres (NS-IC) by contacting neural or neural derived cells with monoclonal antibody 8G1; selecting the cells that bind to this monoclonal antibody; and removing the bound cells, wherein the remaining cells in the population are enriched for human CNS-SC. In various embodiments, the monoclonal antibody may be fluorochrome conjugated or may be conjugated to magnetic particles. Additionally, the selecting may be by fluorescence activated cell sorting, high gradient magnetic selection, or by attachment to and disattachment from the solid phase. In other embodiments, the population containing neural or neural-derived cells is obtained from a neurosphere culture, an adherent culture, or from neural tissue. Alternatively, the method may also involve the step of further enriching the population for CNS-SC by contacting by contacting the remaining cells with a second monoclonal antibody selected from the group consisting of AC133 and 5E12 to produce a population enriched for CNS-SC and selecting those cells that bind to the second monoclonal antibody.

In another aspect, the invention involves a method for producing a population enriched for CNS-SC which can initiate neurospheres (NS-IC) by eliminating cells that are CD24$^+$ from a population of neural or neural-derived cells. This may be accomplished by contacting the population with monoclonal antibody 8G1 and removing those cells that bind to this monoclonal antibody. In one embodiment, the invention also provides a step for further enriching the population by selecting from the remaining population for cells that are AC133$^+$. This may be done, for example, by selecting for cells that bind to monoclonal antibody 5E12.

In a further aspect, the invention involves a method for enriching from a population of neural cells for the populations of neurosphere initiating stem cell (NS-IC) fraction by selecting form the neural cells for cells that bind to monoclonal antibody 8G1 and removing the cells from the population, wherein the remaining cells are enriched in the fraction of NS-IC as compared with the population of neural cells. In various other embodiments, the fraction is further enriched by selecting from the remaining cells for cells that bind to monoclonal antibody AC133 or to monoclonal antibody 5E12.

In yet another aspect, the invention provides a method for isolating a neurosphere initiating stem cell (NS-IC), by selecting from a population of neural or neural-derived cells for cells that are CD24$^+$; eliminating the CD24$^+$ cells from the population; selecting from the remaining population for at least one cells that binds to monoclonal antibody AC133 or monoclonal antibody 5E12; introducing at least one selected cell to a serum-free culture medium containing one or more growth factors selected from the group consisting of LIF, EGF, bFGF, and combinations thereof, and proliferating at least one selected cell in the culture medium.

In still further aspects, the invention provides an antibody that specifically binds to the CD24 antigen, wherein the CD24 antigen specifically binds to the 8G1 antibody. This antibody may be produced by a hybridoma cell line. In some embodiments, this monoclonal antibody may block simultaneous binding to the CD24 antigen by the antibody 8G1.

Also provided is a method for the enrichment of human CNS-SC which can initiate neurospheres (NS-IC) by combining a population of neural or neural-derived cells with a reagent that specifically binds to the CD24 antigen and selecting for those cells that do not bind to the CD24 antigen, wherein the selected cells are enriched for NS-IC. In various embodiments, the reagent may be an antibody. The antibody may be fluorochrome conjugated, wherein the selecting is accomplished by flow cytometry. Alternatively, the antibody may be conjugated to magnetic particles, wherein the selecting is by high gradient magnetic selection.

In another aspect, the invention provides a method for producing a population enriched for human CNS-SC which can initiate neurospheres (NS-IC) by selecting from a population of neural or neural derived cells for cells that are AC133$^+$.

In yet another aspect, the invention involves a method for producing a population enriched for human CNS-SC which can initiate neurospheres (NS-IC) by selecting from neural or neural-derived cells for cells that bind to monoclonal antibody AC133 or to monoclonal antibody 5E12, to produce a population enriched for CNS-SC, wherein the selecting is achieved by attachment to and disattachment from solid phase.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only not intended to be limiting. Other features and advantages of the invention will be apparent from the following detailed description and claims.

DETAILED DESCRIPTION OF THE INVENTION

A population of cells exists within the adult central nervous system (CNS) which exhibit stem cell properties, in their ability to self-renew and to produce the differentiated mature cell phenotypes of the adult CNS. These stem cells are found throughout the CNS, and particularly in the subventricular regions, and dentate gyrus of the hippocampus.

Growth factor-responsive stem cells can be isolated from many regions of the neuraxis and at different stages of development, of murine, rodent and human CNS tissue. These cells vary in their response to growth factors such as EGF, basic FGF (bFGF, FGF-2) and transforming growth factor alpha (TGF$\propto$), and can be maintained and expanded in culture in an undifferentiated state for long periods of time. Both adult and embryonic murine progenitor cells respond to EGF and grow as spheres of undifferentiated cells. These cells show the characteristics of stem cells in that they are multipotent, and under serum containing conditions can differentiate into neurons, astrocytes and oligodendrocytes, as well as maintaining a subpopulation which remains undifferentiated and continues to proliferate under EGF administration. Murine EGF-responsive progenitor cells express mRNA for the EGF receptor in vitro. Human CNS neural stem cell cultures have also been identified. The identification, culture, growth, and use of mammalian, including human, neural stem cell cultures, either as suspension cultures or as adherent cultures, is disclosed in Weiss et al., U.S. Pat. No. 5,750,376 and Weiss et al., U.S. Pat. No. 5,851,832, both incorporated herein by reference. Similarly, Johe, U.S. Pat. No. 5,753,506, also incorporated herein by reference, refers to adherent CNS neural stem cell cultures. When cultured in suspension, CNS neural stem cell cultures typically form neurospheres.

Figure 1:
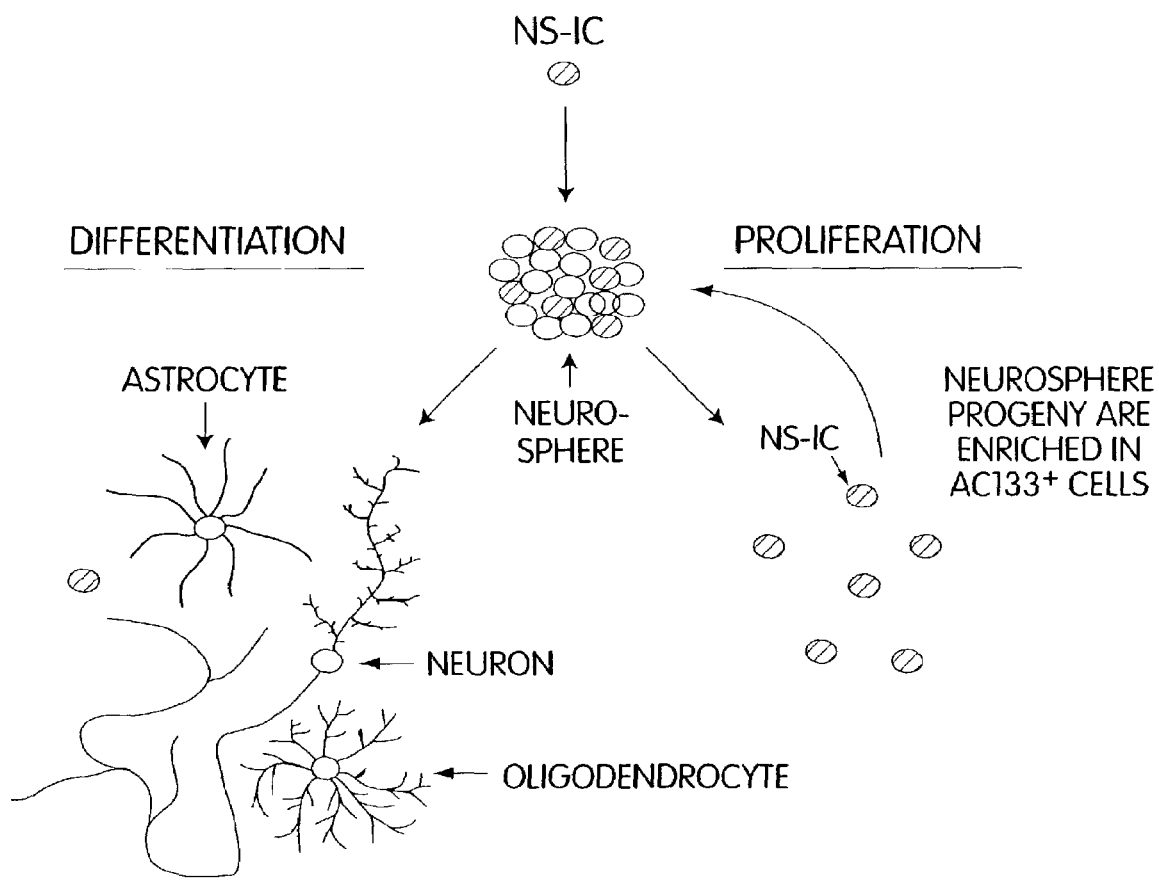
FIG. 1 is a diagram illustrating the proliferation and differentiation of a NS-IC.

FIG. 1 shows the proliferation of a NS-IC as it develops into a neurosphere, and subsequent differentiation into neuron al and glial phenotypes, as well as generation of a progeny NS-IC. In the presence of one or more proliferation-inducing growth factors, the NS-IC divides and gives rise to a sphere of undifferentiated cells composed of more stem cells and progenitor cells (a "neurosphere"). When the clonally derived neurosphere is dissociated and plated as single cells, in the presence of one or more proliferation-inducing growth factors, each NS-IC can generate a new neurosphere. The cells of a single neurosphere are clonal in nature because they are the progeny of a single neural stem cell. In the continued presence of a proliferation-inducing growth factor such as EGF or the like, precursor cells within the neurosphere continue to divide resulting in an increase in the size of the neurosphere and the number of undifferentiated neural cells. The neurosphere is not immunoreactive for glial fibrillary acidic protein (GFAP; a marker for astrocytes), neurofilament (NF; a marker for neurons), neuron-specific enolase (NSE; a marker for neurons) or myelin basic protein (MBP; a marker for oligodendrocytes). However, cells within the neurosphere are immunoreactive for nestin, an intermediate filament protein found in many types of undifferentiated CNS cells (Lehndahl et al., 60 CELL 585–595 (1990), incorporated herein by reference). Antibodies are available to identify nestin, including the rat antibody referred to as Rat401. If the neurospheres are cultured in conditions that allow differentiation, the progenitor cells differentiate to neurons, astrocytes and oligodendrocytes. The mature phenotypes associated with the differentiated cell types that may be derived from the neural stem cell progeny are predominantly negative for the nestin phenotype.

The terminology used for undifferentiated, multipotent, self-renewing, neural cells has evolved such that these cells are now termed "neural stem cells." A neural stem cell is a clonogenic multipotent stem cell which is able to divide and, under appropriate conditions, has self-renewal capability for NS-IC and can include in its progeny daughter cells which can terminally differentiate into neurons, astrocytes, and oligodendrocytes. Hence, the neural stem cell is "multipotent" because stem cell progeny have multiple differentiation pathways. A neural stem cell is capable of self maintenance, meaning that with each cell division, one daughter cell will also be on average a stem cell.

The non-stem cell progeny of a neural stem cell are typically referred to as "progenitor" cells, which are capable of giving rise to various cell types within one or more lineages. The term "neural progenitor cell" refers to an undifferentiated cell derived from a neural stem cell, and is not itself a stem cell. Some progenitor cells can produce progeny that are capable of differentiating into more than one cell type. For example, an O-2A cell is a glial progenitor cell that gives rise to oligodendrocytes and type II astrocytes, and thus could be termed a "bipotential" progenitor cell. A distinguishing feature of a progenitor cell is that, unlike a stem cell, it does not exhibit self maintenance, and typically is thought to be committed to a particular path of differentiation and will, under appropriate conditions, eventually differentiate into glia or neurons.

The term "precursor cells" refers to the progeny of neural stem cells, and thus includes both progenitor cells and daughter neural stem cells.

Cell markers. This invention provides for the identification, isolation, enrichment, and culture of neural stem cells that are capable of forming neurospheres (NS-IC). NS-ICs are identified or selected through the binding of antigens, found on the surfaces of NS-ICs, to reagents that specifically bind the cell surface antigen.

The subject NS-ICs are characterized by their expression of cell surface markers. While it is commonplace in the art to refer to cells as "positive" or "negative" for a particular marker, actual expression levels are a quantitative trait. The number of molecules on the cell surface can vary by several logs, yet still be characterized as "positive". It is also understood by those of skill in the art that a cell which is negative for staining, i.e., the level of binding of a marker specific reagent is not detectably different from a control., e.g. an isotype matched control; may express minor amounts of the marker. Characterization of the level of staining permits subtle distinctions between cell populations.

The staining intensity of cells can be monitored by flow cytometry, where lasers detect the quantitative levels of fluorochrome (which is proportional to the amount of cell surface marker bound by specific reagents, e.g. antibodies). Flow cytometry, or FACS, can also be used to separate cell populations based on the intensity of binding to a specific reagent, as well as other parameters such as cell size and light scatter. Although the absolute level of staining may differ with a particular fluorochrome and reagent preparation, the data can be normalized to a control.

In order to normalize the distribution to a control, each cell is recorded as a data point having a particular intensity of staining. These data points may be displayed according to a log scale, where the unit of measure is arbitrary staining intensity. In one example, the brightest cells in a population are designated as 4 logs more intense than the cells having the lowest level of staining. When displayed in this manner, it is clear that the cells falling in the highest log of staining intensity are bright, while those in the lowest intensity are negative. The "low" staining cells, which fall in the 2–3 log of staining intensity, may have properties that are unique from the negative and positive cells. An alternative control may utilize a substrate having a defined density of marker on its surface, for example a fabricated bead or cell line, which provides the positive control for intensity. The "low" designation indicates that the level of staining is above the brightness of an isotype matched control, but is not as intense as the most brightly staining cells normally found in the population.

As used herein, the terms $AC133^{lo}$ and/or $AC133^{low}$ refer to "low" staining cells, which fall into the $2^{nd}$–$3^{rd}$ log of staining intensity. Those skilled in the relevant arts will recognize that any of the antibodies described herein can also be described using the "lo" or "low" designation (i.e. antibody$X^{lo}$ or antibody$X^{low}$), without altering the intended meaning. Likewise, as used herein, the terms $AC133^{hi}$, $AC133^{high}$, and/or $AC133^{bright}$ refer to those cells in the population designated as 4 logs more intense than the cells having the lowest level of staining. Again, those skilled in the art will recognize that any antibody can be described using these designations, without altering the intended meaning (i.e., antibody$X^{hi}$, antibody$X^{high}$, or antibody$X^{bright}$). The designation antibody$X^{med}$ is intended to refer to an antibody having a staining intensity falling between "low" and "bright".

One of these antigens is an antigen that binds to the AC133 monoclonal antibody. The AC133 antibody (herein referred to as the 5F3 antibody) is exemplary of antibody embodiments of reagents that recognize a human cell marker termed prominin. Prominin is a polytopic membrane protein expressed in various epithelial cells (Weigmann et al., 94(23) Proc Natl Acad Sci USA. 12425–30 (1997); Corbeil et al., 112 (Pt 7) J Cell Sci. 1023–33 (1999); Corbeil et al., 91(7)Blood 2625–6 (1998); Miriglia et al., 91(11) Blood 4390–1 (1998)). Various AC133 antibodies are described in U.S. Pat. No. 5,843,633, incorporated herein by reference. A deposit of the murine hybridoma cell line AC133 was made at the American Type Tissue Collection, 12301 Parklawn Drive, Rockville Md. 20852, on Apr. 24, 1997, and given the ATCC designation HB12346. These AC133 antibodies are capable of immunoselection for the subset of human cells of interest in this invention. Preferred AC133 monoclonal antibodies can be obtained commercially from Miltenyi Biotec Inc. (Auburn Calif.), including AC133/1-PE antibody (Cat #808-01) and AC133/2-PE antibody (Cat #809-01). For MACS separation, a 50:50 mixture of the monoclonal antibodies is preferred. The high tissue specificity of AC133 expression is particularly advantageous during enrichment for highly purified NS-IC populations.

5E12 is a novel monoclonal antibody generated against enzymatically-dissociated human fetal brain cells. The 5E12 monoclonal antibody was generated substantially according to the contralateral immunization method described in Yin, U.S. Pat. No. 5,843,633, incorporated herein by reference. The antigen to which 5E12 binds has a putative MW 125 kD, and is currently believed to be a distinct antigen from prominin.

CD45 is the T200/leucocyte common antigen. Antibodies to CD45 are commercially available from, e.g. Miltenyi Biotec (Auburn, Calif.) (catalog numbers 130-080-201; 130-080-202); Research Diagnostics (Flanders, N.J.) (catalog numbers RDI-M1343clb; RDI-CBL124); RDI-CBL148; RDI-CBL464, etc.). In a preferred embodiment, the cells of this invention and cultures containing them, are additionally characterized (in addition to being prominin positive) as lacking cell surface markers such as CD45.

CD34 is also known as gp105–120. Monoclonal antibodies to CD34 are commercially available from, e.g., Miltenyi Biotec (Auburn, Calif.) (catalog numbers 130-090-954); Research Diagnostics (Flanders, N.J.) (catalog numbers RDI-M1636clb; RDI-CBL128; RDI-CBL496FT; RDI-M2281clb; RDI-CD34-581, etc.). CD34 monoclonal antibodies have been used to quantify and purify lymphohematopoietic stem/progenitor cells for research and for clinical bone marrow transplantation.

CD34 is a monomeric cell surface antigen with a molecular mass of approximately 110 kD that is selectively expressed on human progenitor cells. The gene is expressed by small vessel endothelial cells in addition to hematopoietic progenitor cells and is a single-chain 105–120 kDa heavily O-gylcosylated transmembrane glycoprotein. The sequence is disclosed by Simons et al. (1992) J. Immun. 148:267–271. Antibodies are commercially available, for example, from BD Biosciences, Pharmingen, San Diego, Calif., catalog number 550760.

The monoclonal antibody 8G1 is believed to recognize CD24 (antibodies to CD24 are commercially available), and specifically reacts with the 515 kilodalton α-chain of human LRP/A2MR which is expressed in a restricted spectrum of cell types. A strong immunohistochemical reaction is seen in hepatocytes, tissue macrophages, subsets of neurons and astrocytes in the central nervous system, fibroblasts, smooth muscle cells, and monocyte-derived foam cells in atherosclerotic lesions in the arterial wall. The antibody can also be used for the characterization of a subset of myelomonocytic subtypes of chronic and acute leukemia (CD91). Antibodies to CD91 are commercially available from, e.g., Research Diagnotics (Flanders, N.J.) (catalog numbers RDI-PRO651102; RDI-PRO610102; RDI-PRO61065, etc.).

Other examples of antibodies that recognize CD24 include 32D12 (Diatec (Oslo, NORWAY) (catalog number CD24 3061-ab531)); ALB9 (Accurate Chemical and Scientific Co. (Westbury, N.Y.)); BEK (Miami, Fla.)); Biomeda Corporation, (Foster City, Calif.); Biosource International (Camarillo, Calif. (catalog number AHS2402)); Leinco Technologies (St. Louis, Mo. (catalog numbers C483; C484)); Research Diagnostics, Inc. (Flanders, N.J.)); CLB134 (Accurate Chemical and Scientific Co. (Westbury, N.Y.); Cell Sciences (Norwood, Mass.) (catalog number MON 1119)); CLBGRANBLy1 (Accurate Chemical and Scientific Co. (Westbury, N.Y.); Research Diagnostics, Inc. (Flanders, N.J.)); SN3 (Caltag Laboratories, Inc. (Burlingame, Calif.) (catalog numbers MHCD2400; MHCD2401; MHCD2404)); ML5 (BD Pharmingen (San Diego, Calif.) (catalog numbers 555427; 555428; 555426)); and 24C02 (Lab Vision Corporation (Freemont, Calif.) (catalog number MS-1279); United States Biological (Swampscott, Mass.)).

Cell Deposits. The 5E12.5 and 8G1.7 subject cultures are deposited with ATCC, 10801 University Blvd., Manassas, Va. 20100-2209, under ATCC accession numbers PTA-993 and PTA-994, respectively, in accordance with the provisions of the Budapest Treaty for the Deposit of Microorganisms. Accordingly, all restrictions on the availability to the public of the deposited materials will be irrevocably removed upon the granting of a patent, in accordance with the provisions of the Budapest Treaty for the Deposit of Microorganisms and the provisions of 37 CFR § 1.808(a)(2).

Isolation, enrichment, and selection of cells. The population of cells from which NS-ICs are isolated can be a neural tissue, a population of cells is dissociated from neural tissue, or a population of cells in cell culture, e.g., a cells in a neurosphere culture or an adherent neural stem cell culture.

The invention provides for the isolation and identification of NS-ICs. Identification of a neurosphere initiating stem cell (NS-IC) involves contacting a population of neural cells (or which contains neural or neural derived cells) with a reagent that binds to AC133 antigen and detecting the contact between the reagent that binds to AC133 antigen and the AC133 antigen on the surface of cells. Those cells to which the reagent binds are identified as NS-ICs. The identity of those cells can be confirmed by assays to demonstrate that the cells are in fact NS-ICs, capable of neurosphere initiation, self renewal and multipotency.

The methods of this invention can also be used to isolate $AC133^+$ cells from $AC133^-$ cells using an AC133 antibody, by combining a population of neural cells which contains a fraction of NS-ICs with a reagent that specifically binds to the AC133 antigen, and then selecting for $AC133^+$ cells, to produce a selected population enriched in $AC133^+$ NS-ICs as compared with the population of neural cells before selection.

Accordingly, the invention further provides for the enrichment of NS-ICs from neural tissue or neural stem cell cultures (e.g., neurosphere suspension cultures or neural stem cell adherent cultures). The invention is thus useful for the enrichment of NS-IC from neural tissue in which stem cells and progenitor cells occur at low frequency, or may have been depleted, such as late embryo, juvenile, and adult tissue. One of skill in the art can combine a population of neural cells containing a fraction of NS-ICs with a reagent that specifically binds to the AC133 antigen; and select for the $AC133^+$ cells. In this way, the selected $AC133^+$ cells are enriched in the fraction of NS-IC as compared with the population of neural cells.

The invention also provides an antibody that specifically binds to the CD24 antigen (Gen Bank Accession Number NP-037362), wherein the CD24 antigen specifically binds to the 8G1 antibody. This antibody may be produced by a hybridoma cell line. This monoclonal antibody may block simultaneous binding to the CD24 antigen by the antibody 8G1. Of particular interest are antibodies that bind to the CD24 antigen, cross-reactive antibodies (i.e., those which bind to the same epitope as the 8G1 antigen and substantially inhibits simultaneous binding), species analogs thereof, binding fragments thereof, and conjugates thereof.

Also provided is a method for the enrichment of human CNS-SC which can initiate neurospheres (NS-IC) by combining a population of neural or neural-derived cells with a reagent that specifically binds to the CD24 antigen and selecting for those cells that do not bind to the CD24 antigen, wherein the selected cells are enriched for NS-IC. This reagent may be an antibody. The cell selection can be by any suitable means known in the art, including flow cytometry, such as by fluorescence activated cell sorting using a fluorochrome conjugated AC133 antibody. The selection can also be by high gradient magnetic selection using AC133 antibody is conjugated to magnetic particles. Any other suitable method including attachment to and disattachment from solid phase, is also contemplated within the scope of the invention.

One of skill in the art can derive the population of cells by immunoselection using an AC133 antibody. The population of cells should contain at least 30% $AC133^+$ NS-ICs, preferably at least 50–70% $AC133^+$ NS-ICs, and more preferably greater than 90% $AC133^+$ NS-ICs. Most preferable would be a substantially pure population of $AC133^+$ NS-ICs, comprising at least 95% $AC133^+$ NS-ICs. The degree of enrichment obtained, and actually used, depends on a number of factors, including the method of selection, the method of growth, and the cell dose of the cells that are placed in culture for the initiation of neurospheres.

The population of cells can be derived from late embryo, juvenile, or adult mammalian CNS tissue, or it may be derived from existing cultures of neural stem cells, as described in Weiss, U.S. Pat. No. 5,750,376, or Johe, U.S. Pat. No. 5,753,506. In the most preferred embodiment, the NS-IC are human. In some embodiments, the $AC133^+$ cells in the population can be complexed to endothelial cells.

The in vitro cell cultures described herein containing an enriched population of $AC133^+$ NS-ICs are generally characterized in that the cultures stain positive for nestin and, in the presence of differentiation-inducing conditions, produce progeny cells that differentiate into neurons, astrocytes, and oligodendrocytes.

One of skill in the art can introduce an isolated $AC133^+$ cell to a culture medium, proliferate the isolated $AC133^+$ cell in culture; particularly as a neurosphere; culture the progeny of the isolated $AC133^+$ cell under conditions in which the isolated $AC133^+$ cell differentiates to neurons, astrocytes, and oligodendrocytes; then detect the presence of neurons, astrocytes, and oligodendrocytes. The presence of neurons, astrocytes, and oligodendrocytes characterizes the isolated $AC133^+$ cell as an NS-IC.

Typically $AC133^+$ NS-IC is cultured in a medium that permits the growth and proliferation of neurospheres. The culture in which the isolated $AC133^+$ cell proliferates can be a serum-free medium containing one or more predetermined growth factors effective for inducing multipotent neural stem cell proliferation. The culture medium can be supplemented with a growth factor selected from leukemia inhibitory factor (LIF), epidermal growth factor (EGF), basic fibroblast growth factor (FGF-2; bFGF) or combinations thereof. The culture medium can be further supplemented with neural survival factor (NSF) (Clonetics, Calif.). The conditions in which the $AC133^+$ cell differentiates to neurons, astrocytes, and oligodendrocytes can be culturing the $AC133^+$ cell progeny on a laminin-coated surface in culture medium containing fetal bovine serum (FBS) without EGF, FGF-2 or LIF.

The invention also provides a method for identifying the presence of a growth factor that affects the growth of NS-IC. One of skill in the art combines a composition suspected of containing at least one growth factor that affects the growth of NS-IC with a composition comprising NS-IC, then determines the growth of the NS-IC as a function of the presence of the composition. Altered (increased, decreased, etc.) NS-IC growth indicates the presence in the composition of a growth factor that affects the growth of NS-IC. One can then further identify the growth factor.

Antibodies to AC133. Antibodies to AC133 may be obtained or prepared as discussed in U.S. Pat. No. 5,843,633, incorporated herein by reference. The AC133 antigen can be contacted with an antibody, such as various AC133 monoclonal antibodies, which have specificity for the AC133 antigen. An AC133 antibody is characterized by binding to the AC133 protein under Western blot conditions from reducing SDS-PAGE gels. The AC133 antigen has a molecular weight, based on commercially available standards, in the range of about 117 kDa. The AC133 antigen is expressed on a subset of progenitor cells derived from human bone marrow, fetal bone marrow and liver, cord blood, and adult peripheral blood.

Antibodies to AC133 antigen can be obtained by immunizing a xenogeneic immunocompetent mammalian host (including murine, rodentia, lagomorpha, ovine, porcine, bovine, etc.) with human progenitor cells. The choice of a particular host is primarily one of convenience. A suitable progenitor cell population for immunization can be obtained by isolating CD34$^+$ cells from cytokine mobilized peripheral blood, bone marrow, fetal liver, etc. A suitable progenitor cell population for immunization can be obtained from CNS neural stem cells or other NS-IC. Immunizations are performed in accordance with conventional techniques, where the cells may be injected subcutaneously, intramuscularly, intraperitoneally, intravascularly, etc. Normally, from about $10^6$ to $10^8$ cells will be used, which may be divided up into one or more injections, usually not more than about 8 injections, over a period of from about one to about three weeks. The injections may be with or without adjuvant, e.g. complete or incomplete Freund's adjuvant, specol, alum, etc.

After completion of the immunization schedule, the antiserum may be harvested in accordance with conventional ways to provide polygonal antisera specific for the surface membrane proteins of progenitor cells, including the AC133 antigen. Lymphocytes are harvested from the appropriate lymphoid tissue, e.g. spleen, draining lymph node, etc., and fused with an appropriate fusion partner, usually a myeloma line, producing a hybridoma secreting a specific monoclonal antibody. Screening clones of hybridomas for the antigenic specificity of interest is performed in accordance with conventional methods.

AC133 antibodies can be produced as a single chain, instead of the normal multimeric structure. Single chain antibodies are described in Jost et al., 269 J. BIOL. CHEN. 26267–73 (1994), incorporated herein by reference, and others. DNA sequences encoding the variable region of the heavy chain and the variable region of the light chain are ligated to a spacer encoding at least about 4 amino acids of small neutral amino acids, including glycine or serine. The protein encoded by this fusion allows assembly of a functional variable region that retains the specificity and affinity of the original antibody.

AC133 antibodies can be produced by use of Ig cDNA for construction of chimeric immunoglobulin genes (Liu et al., 84 PROC. NATL. ACAD. SCI. 3439 (1987) and 139 J. IMMUNOL. 3521 (1987), incorporated herein by reference. mRNA is isolated from a hybridoma or other cell producing the antibody and used to produce cDNA. The cDNA of interest may be amplified by the polymerase chain reaction using specific primers (U.S. Pat. No. 4,683,195 and U.S. Pat. No. 4,683,202). Alternatively, a library is made and screened to isolate the sequence of interest. The DNA sequence encoding the variable region of the antibody is then fused to human constant region sequences. The sequences of human constant regions genes may be found in Kabat et al., "Sequences of Proteins of Immunological Interest" N.I.H. PUBLICATION NO. 91-3242 (1991). Human C region genes are readily available from known clones. The chimeric, humanized antibody is then expressed by conventional methods.

AC133 antibodies can be produced as antibody fragments, such as Fv, F(ab')$_2$ and Fab. Antibody fragments may be prepared by cleavage of the intact protein, e.g. by protease or chemical cleavage. Alternatively, a truncated gene is designed. For example, a chimeric gene encoding a portion of the F(ab')$_2$ fragment would include DNA sequences encoding the CH1 domain and hinge region of the H chain, followed by a translational stop codon to yield the truncated molecule.

Immunostaining. Biological samples are assayed for the presence of AC133$^+$ cells by any convenient immunoassay method for the presence of cells expressing the surface molecule bound by the subject antibodies. Assays may be performed on cell lysates, intact cells, frozen sections, etc. The antibodies available from Miltenyi Biotec Inc. (Auburn Calif.) are suitable for the direct immunofluorescent staining of cells.

Cell sorting. The use of cell surface antigens to NS-IC cells provides a means for the positive immunoselection of progenitor cell populations, as well as for the phenotypic analysis of progenitor cell populations using flow cytometry. Cells selected for expression of AC133 antigen may be further purified by selection for other stem cell and progenitor cell markers.

For the preparation of substantially pure progenitor and stem cells, a subset of progenitor cells is separated from other cells on the basis of AC133 binding. Progenitor and stem cells may be further separated by binding to other surface markers known in the art.

Procedures for separation may include magnetic separation, using antibody-coated magnetic beads, affinity chromatography and "panning" with antibody attached to a solid matrix, e.g. plate, or other convenient technique. Techniques providing accurate separation include fluorescence activated cell sorters, which can have varying degrees of sophistication, such as multiple color channels, low angle and obtuse light scattering detecting channels, impedance channels, etc. Dead cells may be eliminated by selection with dyes associated with dead cells (propidium iodide [PI], LDS). Any technique may be employed which is not unduly detrimental to the viability of the selected cells.

Conveniently, the antibodies are conjugated with labels to allow for ease of separation of the particular cell type, e.g. magnetic beads; biotin, which binds with high affinity to avidin or streptavidin; fluorochromes, which can be used with a fluorescence activated cell sorter; haptens; and the like. Multi-color analyses may be employed with the FACS or in a combination of immunomagnetic separation and flow cytometry. Multi-color analysis is of interest for the separation of cells based on multiple surface antigens, e.g. AC133$^+$CD45$^-$, AC133$^-$CD34$^+$, etc. Fluorochro which find use in a multi-color analysis include phycobiliproteins, e.g. phycoerythrin and allophycocyanins; fluorescein and Texas red. A negative designation indicates that the level of staining is at or below the brightness of an isotype matched negative control. A dim designation indicates that the level of staining may be near the level of a negative stain, but may also be brighter than an isotype matched control.

In one embodiment, the AC133 antibody is directly or indirectly conjugated to a magnetic reagent, such as a superparamagnetic microparticle (microparticle). Direct conjugation to a magnetic particle is achieved by use of various chemical linking groups, as known in the art. Antibody can be coupled to the microparticles through side chain amino or sufhydryl groups and heterofunctional crosslinking reagents. A large number of heterofunctional compounds are available for linking to entities. A preferred linking group is 3-(2-pyridyidithio)propionic acid N-hydroxysuccinimide ester (SPDP) or 4-(N-maleimidomethyl)-cyclohexane-1-carboxylic acid N-hydroxysuccinimide ester (SMCC) with a reactive sulfhydryl group on the antibody and a reactive amino group on the magnetic particle.

Alternatively, AC133 antibody is indirectly coupled to the magnetic particles. The antibody is directly conjugated to a hapten, and hapten-specific, second stage antibodies are conjugated to the particles. Suitable haptens include digoxin, digoxigenin, FITC, dinitrophenyl, nitrophenyl, avidin, biotin, etc. Methods for conjugation of the hapten to a protein, i.e. are known in the art, and kits for such conjugations are commercially available.

To practice the method, the AC133 antibody is added to a cell sample. The amount of AC133 Ab necessary to bind a particular cell subset is empirically determined by performing a test separation and analysis. The cells and AC133 antibody are incubated for a period of time sufficient for complexes to form, usually at least about 5 min, more usually at least about 10 min, and usually not more than one hr, more usually not more than about 30 min.

The cells may additionally be incubated with antibodies or binding molecules specific for cell surface markers known to be present or absent on progenitor or stem cells.

The labeled cells are separated in accordance with the specific antibody preparation. Fluorochrome labeled antibodies are useful for FACS separation, magnetic particles for immunomagnetic selection, particularly high gradient magnetic selection (HGMS), etc. Exemplary magnetic separation devices are described in WO 90/07380, PCT/US96/00953, and EP 438,520. The AC133 Cell Isolation Kit (Miltenyi Biotec Inc., Auburn Calif.) can be used for the positive selection of AC133$^+$ cells. The kit provides a tool for single step isolation of AC133$^+$ cells. The AC133 Cell Isolation Kit contains FcR Blocking Reagent and MACS colloidal MicroBeads conjugated to the monoclonal mouse anti-human AC133 antibody.

The purified cell population may be collected in any appropriate medium. Various media are commercially available and may be used, including Dulbecco's Modified Eagle Medium (dMEM), Hank's Basic Salt Solution (HBSS), Dulbecco's phosphate buffered saline (dPBS), RPMI, Iscove's modified Dulbecco's medium (IMDM), phosphate buffered saline (PBS) with 5 mM EDTA, etc., frequently supplemented with fetal calf serum (FCS), bovine serum albumin (BSA), human serum albumin (HSA), etc.

Populations highly enriched for human progenitor or stem cells are achieved in this manner. The desired cells will be 30% or more of the cell composition, preferably 50% or more of the cell population, more preferably 90% or more of the cell population, and most preferably 95% or more (substantially pure) of the cell population.

Use of purified stem cell/progenitor cells. The AC133$^+$ stem cells/progenitor cells are useful in a variety of ways. The AC133$^+$ cells can be used to reconstitute a host whose cells have been lost through disease or injury. Genetic diseases associated with cells may be treated by genetic modification of autologous or allogeneic stem cells to correct a genetic defect or treat to protect against disease. Alternatively, normal allogeneic progenitor cells may be transplanted. Diseases other than those associated with cells may also be treated, where the disease is related to the lack of a particular secreted product such as hormone, enzyme, growth factor, or the like. CNS disorders encompass numerous afflictions such as neurodegenerative diseases (e.g. Alzheimer's and Parkinson's), acute brain injury (e.g. stroke, head injury, cerebral palsy) and a large number of CNS dysfunctions (e.g. depression, epilepsy, and schizophrenia). In recent years neurodegenerative disease has become an important concern due to the expanding elderly population which is at greatest risk for these disorders. These diseases, which include Alzheimer's Disease, Multiple Sclerosis (MS), Huntington's Disease, Amyotrophic Lateral Sclerosis, and Parkinson's Disease, have been linked to the degeneration of neural cells in particular locations of the CNS, leading to the inability of these cells or the brain region to carry out their intended function. By providing for maturation, proliferation and differentiation into one or more selected lineages through specific different growth factors the progenitor cells may be used as a source of committed cells. Neurospheres can also be used to produce a variety of blood cell types, including myeloid and lymphoid cells, as well as early hematopoietic cells (see, Bjornson et al., 283 SCIENCE 534 (1999), incorporated herein by reference).

The AC133$^+$ cells may also be used in the isolation and evaluation of factors associated with the differentiation and maturation of cells. Thus, the cells may be used in assays to determine the activity of media, such as conditioned media, evaluate fluids for growth factor activity, involvement with dedication of lineages, or the like.

The AC133$^+$ cells may be frozen at liquid nitrogen temperatures and stored for long periods of time, being thawed and capable of being reused. The cells will usually be stored in 5% DMSO and 95% fetal calf serum. Once thawed, the cells may be expanded by use of growth factors or stromal cells associated with stem cell proliferation and differentiation.

The following examples are presented in order to more fully illustrate the preferred embodiments of the invention. These examples should in no way be construed as limiting the scope of the invention, as defined by the appended claims.

EXAMPLE 1

AC133 Magnetic Cell Sorting (MACS) Positive Selected Fetal Brain Cells Contain Neurosphere Initiating Cell (NS-IC) Activity AC133$^+$ cells are prepared by the following method: Human fetal brain (FBR 10–20 gestational week ["g.w."]) were obtained from Advanced Bioscience Resources, INC (Oakland, Calif.) after obtaining informed consent. Human fetal brain tissues were cut into 1–3 mm cubed pieces using scalpels, transferred into 50 mL centrifuge tubes and wash once with 0.02% EDTA/PBS solution. Tissues were dissociated enzymatically in the presence of collagenase and hyaluronidase at 37° C. for 1 hr. Debris and aggregates were removed by filtering cell suspensions through 70 micron filter cup.

AC133$^+$ human fetal brain cells were separated by using paramagnetic antibody microbeads, AC133/1 Cell isolation Kit (Cat. #508-01, Miltenyi Biotec, Auburn, Calif.). MACS separations were performed based on instruction accompanied with the kit. In a representative flow cytometric MACS separation from a typical AC133$^+$ isolation, about 44% of the cells were AC133$^+$CD45$^-$, while about 2% were CD34$^+$ (These CD34$^+$ cells were endothelial cells complexed to the purified NS-IC).

The AC133$^+$ selected cells which resulted from the method described above (using brain 18 g.w.) were still heterogeneous. The cells tended to form a complex with endothelial cells. Endothelial cells were identified as CD34$^+$ or CD105$^+$. AC133 MACS separation also enriches CD34$^+$ endothelial cells which are associated with AC133⁺ cells. (After passaging, the NS-IC separate from the complexed endothelial cells and purified NS-IC can be obtained.)

AC133⁺ MACS separated cells were cultured in the presence of media containing EGF, FGF-2, and LIF, as described above. In general, cells from early gestational age fetal brain (5–12 g.w.) were enriched for NS-IC and no enrichment was required to initiate neurosphere cultures. On the other hand, cells from older fetal brain samples (16–20 g.w.) contained far less NS-IC activity and required enrichment for initiating neurosphere cultures. In other words, AC133⁺ is useful for the enrichment of NS-IC from older gestational age humans brain tissue. AC133⁺ MACS separated cells from fetal brain (18 g.w.) were enriched for NS-IC activity, while whole human fetal brain cells (18 g.w.) without AC133⁺ MACS separation failed to initiate neurosphere cultures.

Neurosphere cells established from AC133 MACS cells express nestin, as tested after ~7 days in culture and detected by rabbit anti-human nestin polyconal antibodies. For example, among the neurosphere cells available from Cyto-Therapeutics (Providence, R.I.), FBR 1069 (18 g.w.) and FBR 1070 (20 g.w.) expressed nestin. When induced to differentiate, the AC133⁺ MACS-derived neurosphere cells could differentiate into neurons and astrocytes, as detected by β-tubulin staining for neurons and GFAP staining for astrocytes. In this particular differentiation assay, neurosphere cells were cultured onto a laminin-coated surface in the presence of 1% FBS and without EGF, FGF-2 and LIF.

Other differentiation assay can be used to induce differentiation of NS-IC to neurons, astrocytes and oligodendrocytes.

EXAMPLE 2

AC133 is a Critical Cell Surface Marker Expressed on Cells from Long-Term Neurosphere Culture A long-term neurosphere cell culture, 8.5 FBR, was obtained from CytoTherapeutics Inc. (Providence, R.I.). The 8.5 FBR neurosphere cells express AC133 relatively uniformly. These 8.5 FBR cells are also Thy-1⁺, CD166⁺, and HLA-DR⁺. When Ex Vivo 15 was used as basal media, higher percentage of neurosphere cultures initiated from primary brain tissue from 18 g.w. It is therefore possible to evaluate AC133⁺ fraction of cells in developing neurosphere cultures. The proportion of AC133⁺ cells increased as neurosphere developed. Once neurosphere cells were well established, virtually all cells forming neurospheres expressed AC133.

EXAMPLE 3

Neurosphere Initiating Cells can be Separated Using Monoclonal Antibody, AC133: Flow Cytometry Cell Sorting (FACS) Approach The purpose of this EXAMPLE is to test whether AC133⁺ cells were the only cells in the brain that have pluripotent NSC activity. The monoclonal antibody (mAb) against human CD45 was used to exclude blood cell contamination in fetal tissue. In some cases, mAb against human CD34 was also used to exclude endothelial cells and endothelial-neural progenitor complexes. The fetal brain cells were thus defined as CD45⁻CD34⁻. To measure neural stem cells and primitive progenitor activities, a NS-IC assay was established to determine frequency of NS-IC in a given population. When NS-IC are rare and express AC133 antigen uniformly, NS-IC can be enriched by AC133⁺ selection, and correspondingly depleted in other fractions.

Source of monoclonal antibodies: AC133 antigen was defined by two mAbs AC133/1 and AC133/2, both conjugated with phycoerythrin, which are available through Miltenyi Biotec (Auburn, Calif.). Antihuman CD45-FITC and Glycophrin A-FITC were obtained from CALTAG (Burlingame, Calif.) and Coulter (Miami, Fla.) respectively. Anti-human allophycocyanin-conjugated CD34 was obtained from BDIS (San Jose, Calif.).

Cell preparation: FBR were dissociated by collagnease and hyaluronidase, and still contained endothelial-progenitor complex, which prevented the isolation of a candidate of NSC in single cell suspension (endothelial cells are CD45⁺). To dissociate this endothelial cell-NS-IC complex, FBR cells processed as described above, were further treated with trypsin for 10–15 min. The AC133 antigen, CD45 antigen and CD34 antigen were resistant for trypsin treatment, while Glycophrin A was sensitive.

After trypsin digestion, cells were washed and stained with mAbs against CD45, Glycophrin A, AC133 and CD34. No immunomagnetic bead selections were used. The cells were incubated for 20–60 min on ice. After the final wash, the cells were resuspended in HBSS solution containing 1 μg/mL propidium iodine (PI). The labeled cells were analyzed and sorted with a dual-laser FACS (Becton Dickinson, San Jose). Dead cells were excluded from analysis by their PI staining characteristics. After sorting purity of sorted cell populations were checked by FACS reanalysis. A representative FACS profiles of before sorting and post-sorting of AC133⁺CD45⁻ cells (NS-IC, 5% of the starting cells) and AC133⁻ CD45⁻ cells (~87% of the starting cells) was performed.

NS-IC activity is highly enriched in the AC133⁺ but not the AC133⁻ subset: FBR cells (typically 16–20 g.w.) were typically sorted for CD45⁻CD34⁻AC133⁻ and CD45⁻CD34⁻ AC133⁻ fractions. No significant NS-IC activity resided in CD45⁺ or CD45⁻CD34⁺ populations in FBR.

The sorted cells were cultured in the neurosphere media described above. Typically, Ex Vivo 15 or combination of Ex Vivo 15, D-MEM, F-12 media were used as a basal medial. To maximize neurosphere development, the sorted cells were typically cultured in the presence of LIF, FGF-2, EGF and neural survival factor, NSF (Cat. CC-4323, Clonetics, San Diego, Calif.).

A single cell suspension was obtained after cell sorting. After 4–5 days in vitro culture, the AC133⁺ cells started to proliferate and small neurospheres were observed 8–10 days post culture initiations. The cells could initiate neurospheres when cultured in the presence of LIF, FGF-2, EGF without NSF. Neurosphere cultures were initiated from four out of four FBR tissues (18–20 g.w.) sorted for AC133⁺CD45⁻ or AC133⁺CD45⁻CD34⁻.

In contrast, when AC133⁻CD45⁻ FBR cells were placed in culture in the presence of LIF, FGF-2, and EGF, very few neurosphere formations were seen, and failed to passage to a new flask. When additional NSF was added in the growth media, some neurosphere initiation was observed. Thus, AC133⁻CD45⁻ FBR cells were depleted in a significant amount of NS-IC.

EXAMPLE 4

AC133+ Cell Separation to Enrich for NS-IC Cells

AC133+ cell separation can effectively be used to enrich for NS-IC cells from tissue. Furthermore AC133+ cell separation can further enrich for NS-IC cells from established preparations. In one test, AC133+ cell sorting of dissociated neurospheres (CytoTherapeutics, Providence, R.I.) provides a greatly enriched NS-IC culture and shows increased neurosphere establishment. Using that culture, the cell dose required to initiate a neurosphere in each well (i.e., 100% positive) can be reduced from 3,000–10,000 cells to about 30 cells (see, TABLE 1, below).

(FBR 1104 AC133 neg. selected cells), establishment of neurosphere cultures from those populations is markedly reduced.

Quantitative NS-IC assay: To assay for the presence of NS-IC, cell populations suspected of containing the multipotent NS-IC are subjected to clonal development. Cells are grown in proliferation medium to form neurospheres, then induced to differentiate to form neurons, astrocytes, and oligodendrocytes. The presence of neurons, astrocytes, and oligodendrocytes can be shown by immunostaining. For example, neurons stain for the presence of β-tubulin; astrocytes stain for the presence of GFAP; and oligodendrocytes stain for the presence of O4.

TABLE 1

| Tissue ID | Cell | Cell Dose | Score | #Well | % Positive | % Negative |
| --- | --- | --- | --- | --- | --- | --- |
| FBR 1104 | Post trypsin | 1,000 | 6 | 24 | 25.0% | 75.0% |
|  | Ex Vivo 15 | 3,000 | 20 | 24 | 83.3% | 16.7% |
|  | LIF/EGF/FGF-2 | 10,000 | 24 | 24 | 100.0% | 0.0% |
|  |  | 30,000 | 12 | 12 | 100.0% | 0.0% |
|  |  | 100,000 | 12 | 12 | 100.0% | 0.0% |
| FBR 1104 | Post trypsin | 1,000 | 23 | 24 | 95.8% | 4.2% |
|  | Ex Vivo 15 | 3,000 | 24 | 24 | 100.0% | 0.0% |
|  | LIF/EGF/FGF-2/NSF | 10,000 | 24 | 24 | 100.0% | 0.0% |
|  |  | 30,000 | 12 | 12 | 100.0% | 0.0% |
|  |  | 100,000 | 12 | 12 | 100.0% | 0.0% |
| FBR 1104 | AC133 neg. selected cells | 1,000 | 0 | 24 | 0.0% | 100.0% |
|  | Ex Vivo 15 | 3,000 | 1 | 24 | 4.2% | 95.8% |
|  | LIF/EGF/FGF-2/NSF | 10,000 | 28 | 48 | 58.3% | 41.7% |
|  | AC133+ selected cells | 10 | 2 | 24 | 8.3% | 91.7% |
|  | Ex Vivo 15 | 100 | 24 | 24 | 100.0% | 0.0% |
|  | LIF/EGF/FGF-2/NSF | 300 | 24 | 24 | 100.0% | 0.0% |
|  |  | 1,000 | 24 | 24 | 100.0% | 0.0% |
| FBR 1101 | Post trypsin | 1,000 | 9 | 24 | 37.5% | 62.5% |
|  | Ex Vivo 15 | 3,000 | 16 | 24 | 66.7% | 33.3% |
|  | LIF/EGF/FGF-2 | 10,000 | 23 | 24 | 95.8% | 4.2% |
|  |  | 30,000 | 12 | 12 | 100.0% | 0.0% |
|  |  | 100,000 | 12 | 12 | 100.0% | 0.0% |
| FBR 1101 | Post trypsin | 1,000 | 16 | 24 | 66.7% | 33.3% |
|  | Ex Vivo 15 | 3,000 | 21 | 24 | 87.5% | 12.5% |
|  | LIF/EGF/FGF-2/NSF | 10,000 | 24 | 24 | 100.0% | 0.0% |
|  |  | 30,000 | 12 | 12 | 100.0% | 0.0% |
|  |  | 100,000 | 12 | 12 | 100.0% | 0.0% |
| FBR 1101 | AC133+ selected cells | 1 | 9 | 96 | 9.4% | 90.6% |
|  | Ex Vivo 15 | 10 | 42 | 60 | 70.0% | 30.0% |
|  | LIF/EGF/FGF-2/NSF | 30 | 23 | 24 | 95.8% | 4.2% |
|  |  | 100 | 11 | 12 | 91.7% | 8.3% |

As shown in TABLE 1, the non-enriched fresh brain tissue ("FBR") used here (g.w. 20) may contain NS-IC in such numbers that it requires a cell dose of between 3,000 and 10,000 cells to initiate neurospheres in every well. By using the method of the invention, enriched populations can be obtained, such that a cell dose of 1,000 cells or less is required, and more preferably an enriched population such that a cell dose of less than 100 cells is required. As shown in TABLE 1, enrichment here has been achieved so that a cell dose of only about 30 cells is required per well to establish a neurosphere culture in each well. TABLE 1 also shows that when populations are depleted in AC 133+ cells The quantitative NS-IC assay can be performed on unpurified tissue cells, on AC133+ sorted cells, and on clonal neurosphere cell lines.

EXAMPLE 5

Cell Culture Media for Growth and Passage of NS-IC

Weiss et al., U.S. Pat. No. 5,750,376 and Weiss et al., U.S. Pat. No. 5,851,832 disclose "culture medium containing one or more predetermined growth factors effective for inducing multipotent neural stem cell proliferation" and "differentiation-inducing conditions". However, different basal media can be used, including, but not limited to:

D-MEM/F12 (Gibco BRL, Gaithersburg, Md.);

Ex Vivo 15 (Bio Whittaker, Walkersville, Md.);

Neural progenitor basal media, (Clonetics. San Diego, Calif.); or combination of the basal media listed above.

A typical media formulation to culture human neurosphere cells is provided in TABLE 2.

TABLE 2

Serum-Free N2/EGF Supplemented Culture Medium For Neurospheres

| Quantity | Reagents |
|---|---|
| 87 ml | DMEM/F12 (Gibco lot. 1012915; Cat. No. 11330-032) |
| 1 ml | N-2 Supplement (Gibco lot 1017018; Cat. No. 17502-014) |
| 1 ml | 0.2 mg/ml heparin (Sigma lot 28H0320; Cat. No. H-3149) |
| 1 ml | 0.2 M Glutamine (JCR lot 7N2320; Cat. No. 59202-77p) |
| 10 ml | 3% Glucose (Sigma, lot 37H0841; Cat. No. G-7021) |
| 20 µl | 100 µg/ml EGF (R&D lot CE107091; Cat. No. 236-EG) |
| 100 µl | 20 µg/ml FGF-2 (Gibco lot KCQ411; Cat. No. 13256-029) |
| 100 µl | 10 µg/ml LIF (R&D lot OX038021; Cat. No. 250-L) |

EGF is added to 100 ml base medium for human neurospheres after filtering the medium. EGF is relatively stable in the medium. FGF-2 and LIF are added when medium is ready to use. The final concentrations of the supplement reagents are:

| | |
|---|---|
| 5 µg/ml | Insulin |
| 100 µg/ml | Human transferrin |
| 6.3 ng/ml | Progesterone |
| 16.1 µg/ml | Putrascine |
| 5.2 ng/ml | Selenite |
| 20 ng/ml | EGF |
| 20 ng/ml | FGF-2 |
| 10 ng/ml | LIF |
| 2 µg/ml | heparin |
| 2 mM | L-glumtamine |
| 6 mg/ml | Glucose |

The optimization of media formulation permits a higher percentage of neurospheres initiated from primary brain tissue to be established. We prefer Ex Vivo 15 media. The optimization of media formulation also permits a more consistent growth of neurospheres. To maximize neurosphere development, the NS-IC are typically cultured in the presence of LIF, bFGF, EGF and neural survival factor, NSF (Cat. CC-4323, Clonetics, San Diego, Calif.). In one test, both trypsinized FBR 1101 neural cells and trypsinized FBR 1104 neural cells (CytoTherapeutics, Providence, R.I.), show increased growth when cultured in Ex Vivo 15 medium with LIF, bFGF, EGF, and NSF.

EXAMPLE 6

Direct Isolation of Human Neural Stem Cells from Fetal Brain by Cell Sorting

A large source of highly defined engraftable human cells capable of extensive neuron al regeneration could be an effective therapeutic product for the treatment of neurodegenerative disorders. To define reproducible methods for the enrichment of human neural stem cells (NSCs), monoclonal antibodies (mAbs) directed toward surface markers on human neural cells to identify and purify NSCs by fluorescence activated cell sorting (FACS) were developed and used. Based on FACS and immunohistochemical analyses, two mAbs, 5F3 and 5E12 were identified. They defined small subsets of fetal brain cells and displayed specific reactivity to cells in the floor plate and ependymal layer of the spinal cord (12 g.w.), sites known to contain CNS stem cells. These mAbs, stain less than 5% of FBR cells, and greater than 95% of cells from long-term neurosphere cultures were positive.

As an example, two cell populations 5F3+CD34−CD45− (5F3+) and 5F3−CD34−CD45−(5F3−) were sorted and tested for their ability to initiate neurosphere cultures. The 5F3+ subset was highly enriched for neurosphere-initiating cell activity; they proliferated to form small neurosphere by 8–10 days in culture. In contrast, the sorted 5F3− cells remained as a single cell suspension, failed to initiate neurospheres, and eventually died. The expanded 5F3+ sorted neurosphere cells were positive for nestin expression, and differentiated into neurons and glia following exposure to differentiation conditions. Using the NOD SCID mouse, in vivo studies show that at 8 weeks post transplantation the 5F3+ neurosphere cells can engraft and migrate. These studies show that human NSCs have been identified and enriched based on cell surface markers and flow cytometry and their activity has been demonstrated using in vitro and in vivo assays.

Figure 5:
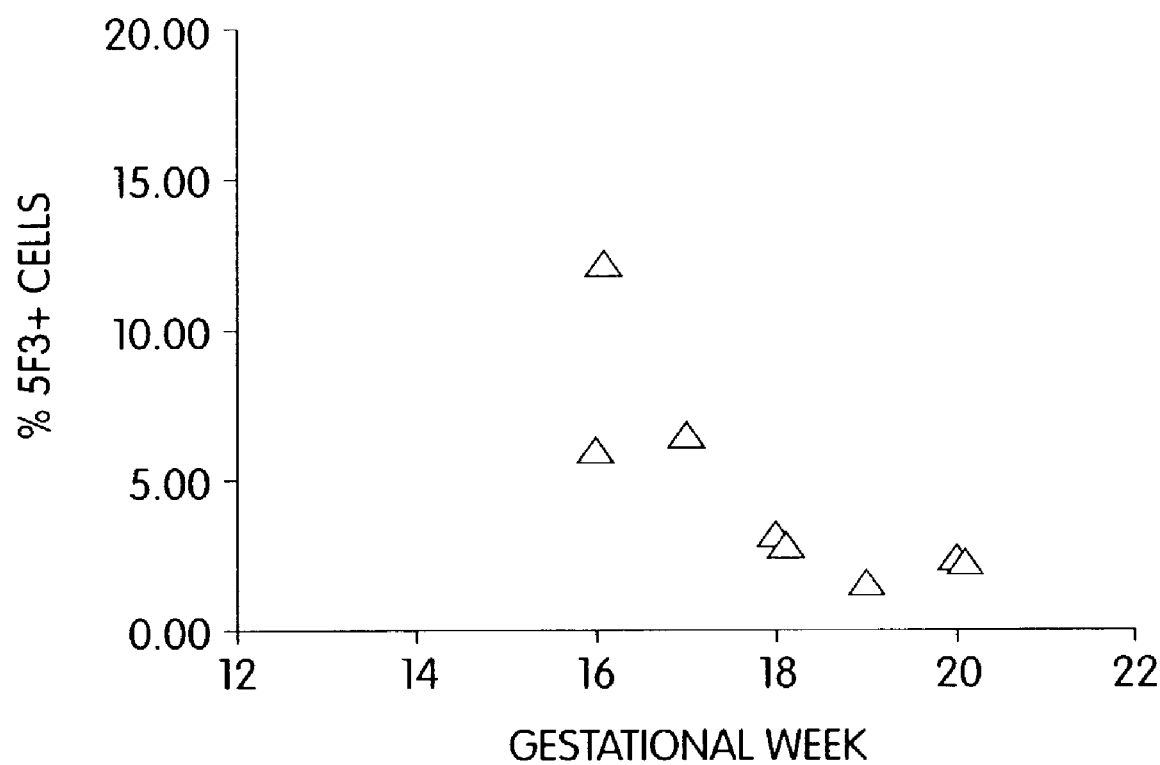
FIG. 5 is a chart showing the distribution of 5F3+ cells in fetal brain as a function of gestational age.

In further experiments, brain and spinal cord tissues over various gestational ages were examined. The earlier (5–12 g.w.) gestational ages have a higher frequency of neurosphere initiating cell (NS-IC) than later gestational ages (16–20 g.w.). See, e.g., FIG. 5. Direct culturing of cells derived from these tissues leads to neurosphere initiation.

The data (shown in the Table below) demonstrate that cell population of neural cells enriched for $5F3^+$ cells are enriched for NS-IC activity, as much as 23 fold.

| Population | % in brain | NS-IC | Range |
|---|---|---|---|
| Post processed brain cells (n = 8) | 100 | 1/819 | 1/304–1435 |
| 5F3− sorted (n = 6) | 95 | 1/5434 | 1/4224–7772 |
| 5F3+ sorted (n = 6) | 4.6 | 1/36 | 1/10–74 |

Figure 2:
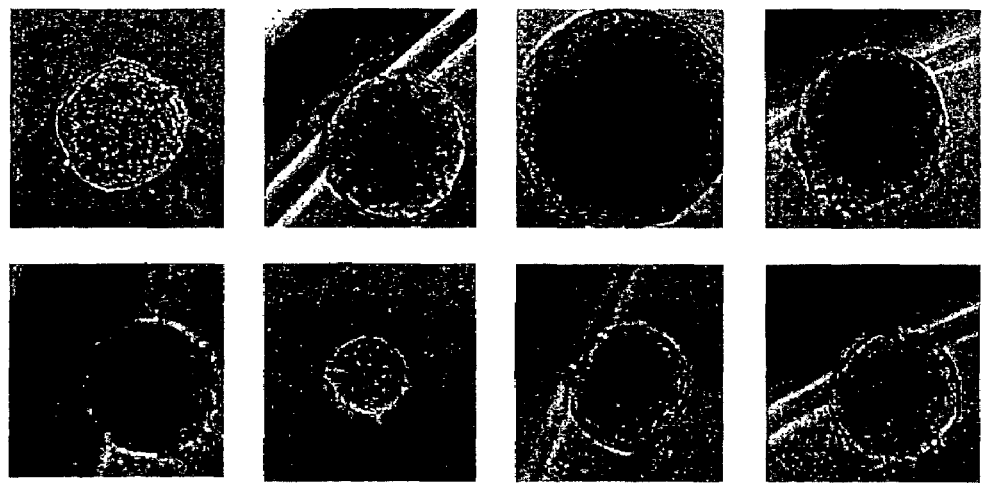
FIG. 2 is a series of photographs showing that neurosphere cultures can be initiated from single-cell sorted 5F3$^+$ cells.

Further, as FIG. 2 shows, neurospheres can be derived from single-cell sorted $5F3^+$ cells. It has also been demonstrated that self-renewal of neurosphere cells derived from $5F3^+$ sorted cells can be achieved by re-initiation of neurospheres from single cells. Conversely, the data indicates that cell populations depleted of $5F3^+$ cells are also depleted for NS-IC activity.

EXAMPLE 7

Isolation of NS-IC by Different Markers

Figure 3:
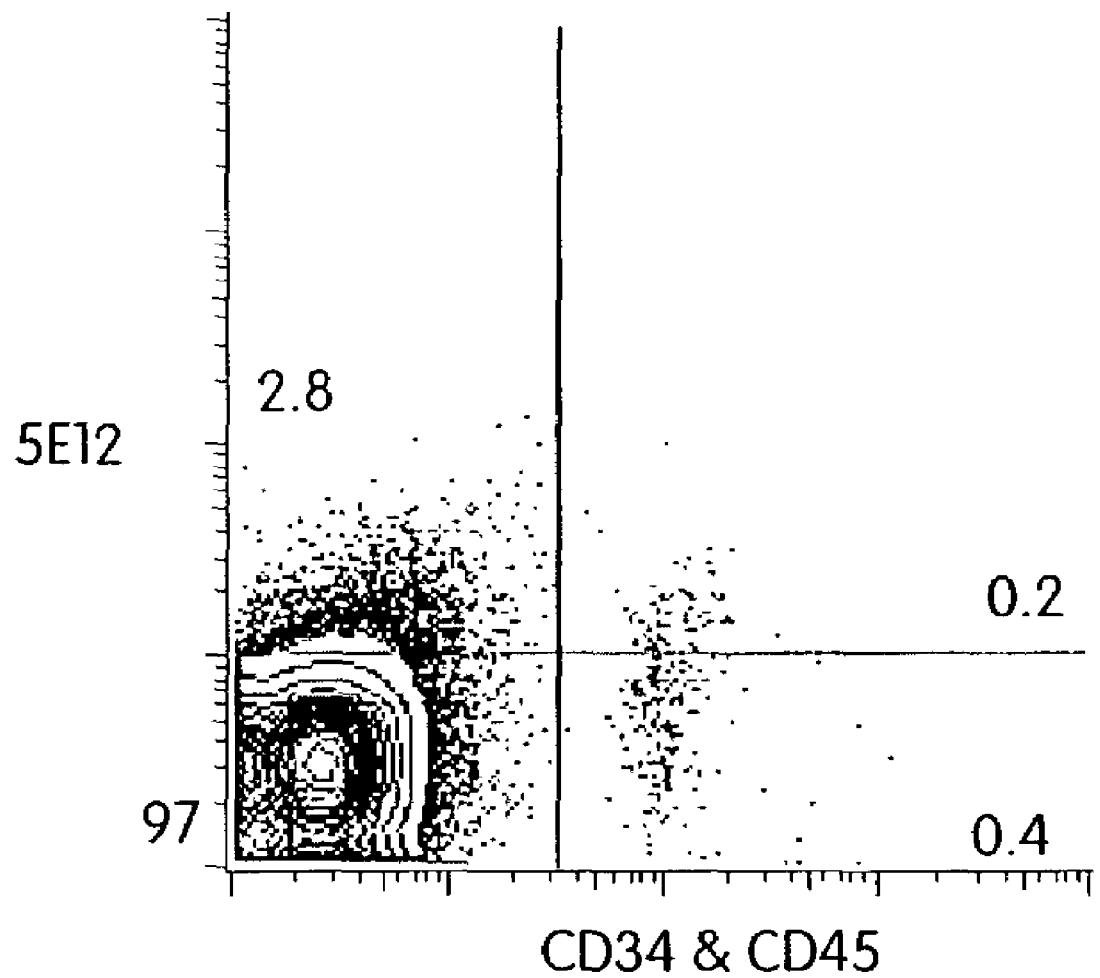
FIG. 3 is a dot plot of fluorescence activated cell sorting (FACS) data showing the isolation of human CNS neural stem cells using cell surface markers using the monoclonal antibody 5E12. The x axis represents cell staining for antibodies to CD34 and CD45. The y axis represents cell staining with the 5E12 antibody.
Figure 4B:
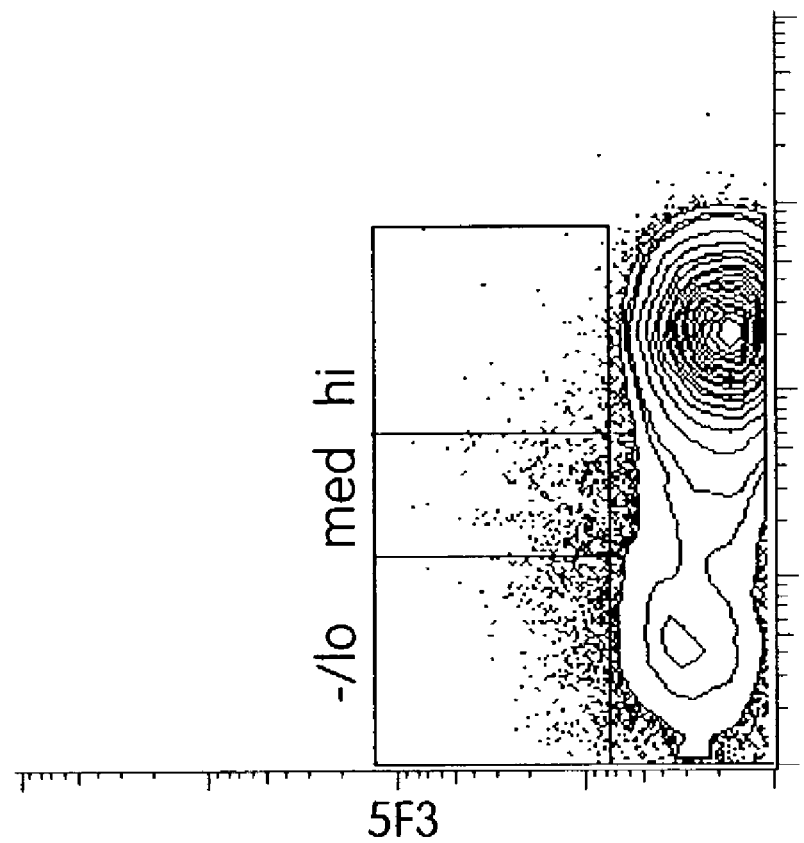
FIG. 4 is a two panel dot plot of FACS sorting data showing the isolation of human neural stem cells by cell surface markers. Panel A shows that 5F3$^+$ cells co-express the antigen for the 5E12 antibody. Panel B shows that 5F3$^+$ cells typically do not express the antigen for the 8G1 antibody.
Figure 4A:
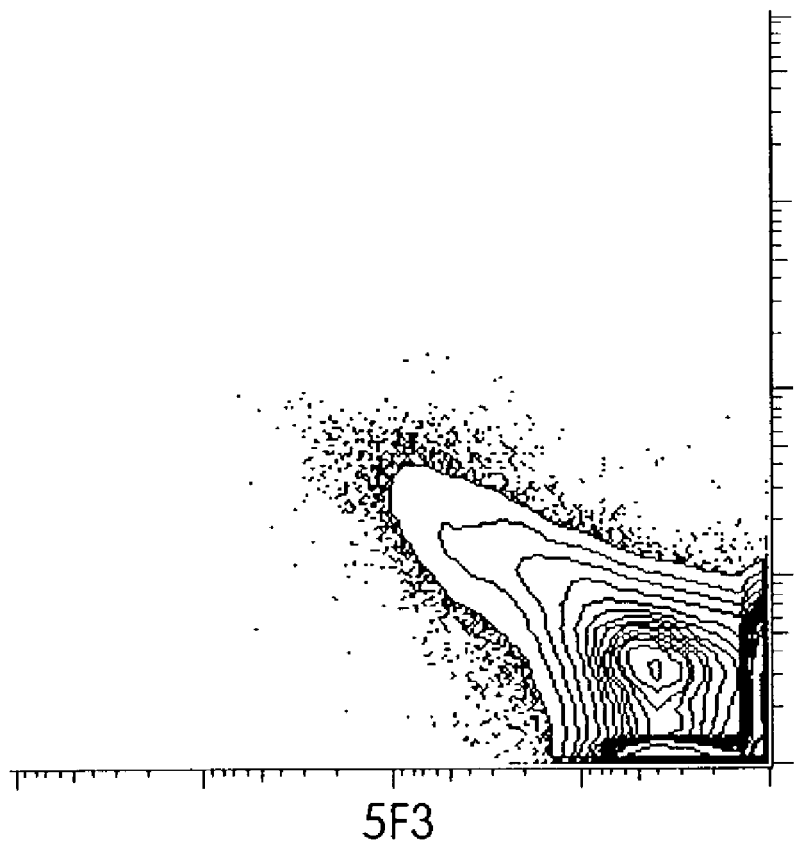

As a second example, cell populations using a novel monoclonal antibody, 5E12, described herein were sorted. The $5E12^+$ subset was enriched for neurosphere-initiating cell activity, as shown in the Table below. See also FIG. 3. The data suggests that the antigen to the 5E12 antibody is coexpressed with the AC133 antigen on $5F3^+$ cells.

The 8G1 monoclonal antibody was also evaluated as a subselector for neural stem cells, as shown in the Table below. Cells that were $5F3^+$ and $8G1^{-/lo}$ displayed more stem cell-like properties, while cells that were $5F3^+$ and $8G1^{med/hi}$ displayed more progenitor cell-like properties.

ENRICHMENT OF NS-IC BY 5F3, 5E12 AND 8G1 ANTIBODIES

| Population | % in brain | NS-IC | Range |
| --- | --- | --- | --- |
| Brain cells control (n = 8) | 100 | 1/819 | 1/304–1435 |
| 5F3– sorted (n = 6) | 95 | 1/5434 | 1/4224–7772 |
| 5F3+ (n = 6) | 4.6 | 1/36 | 1/10–74 |
| 5E12– (n = 2) | 97 | 1/1335 | 1/1259, 1411 |
| 5E12+ (n = 3) | 2.5 | 1/286 | 1/79–392 |
| 5F3+ 8G1$^{-/lo}$ (n = 3) | 1.1 | 1/23 | 1/15–34 |
| 5F3+ 8G1$^{mid/hi}$ (n = 3) | 1.7 | 1/63 | 1/38–105 |

*All sorted populations were CD34$^-$ CD45$^-$

EXAMPLE 8

In vivo Studies NS-IC

Figure 6:
FIG. 6 is a series of photographs showing results of the transplantation of human neural cells into NOD SCID mouse.
Figure 6:
Figure 7:
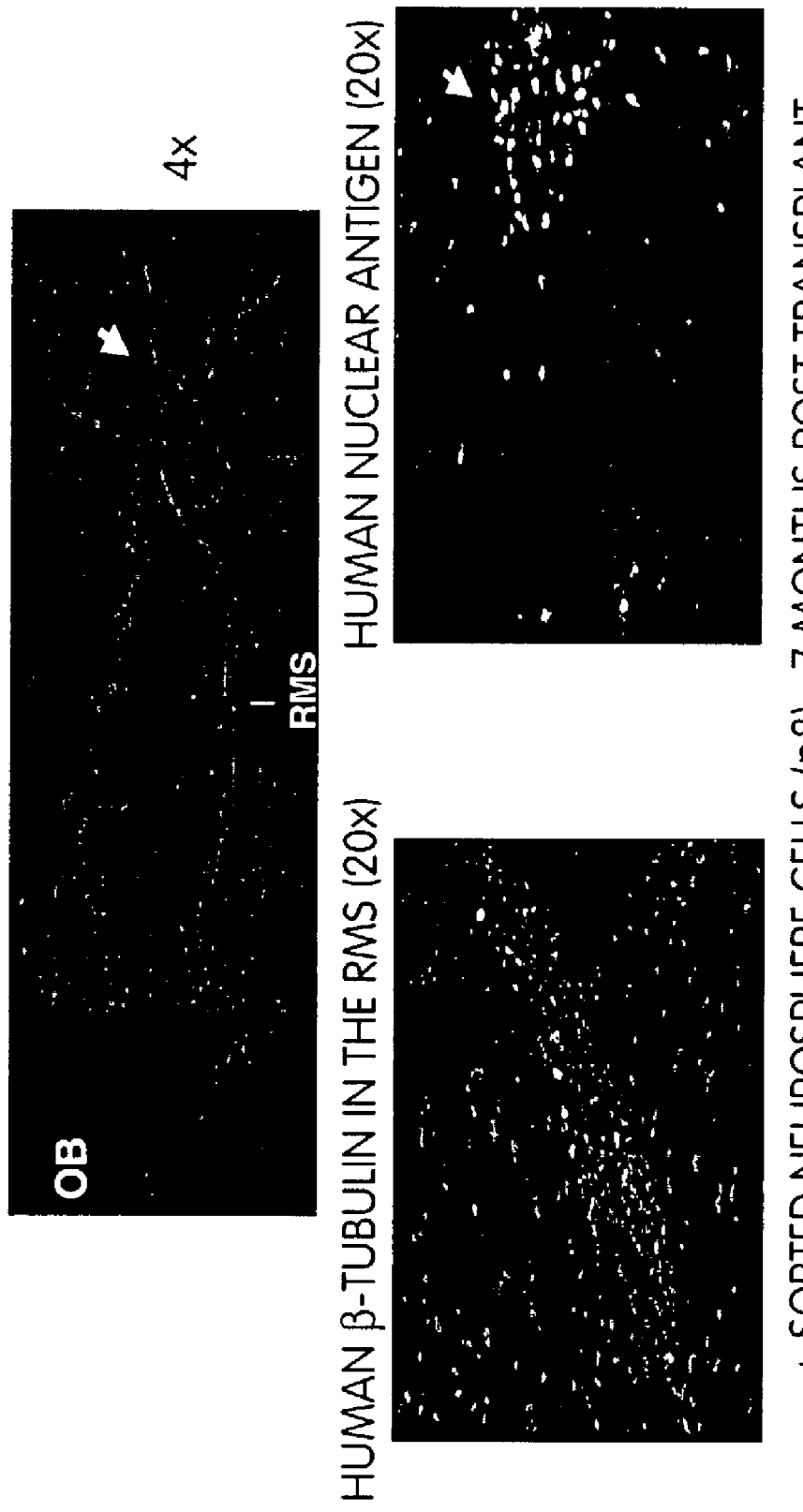
FIG. 7 is a series of photographs showing that the progeny of 5F3+ sorted cells migrate through the rostral migratory stream (RMS) when transplanted into a rodent model.
Figure 8:
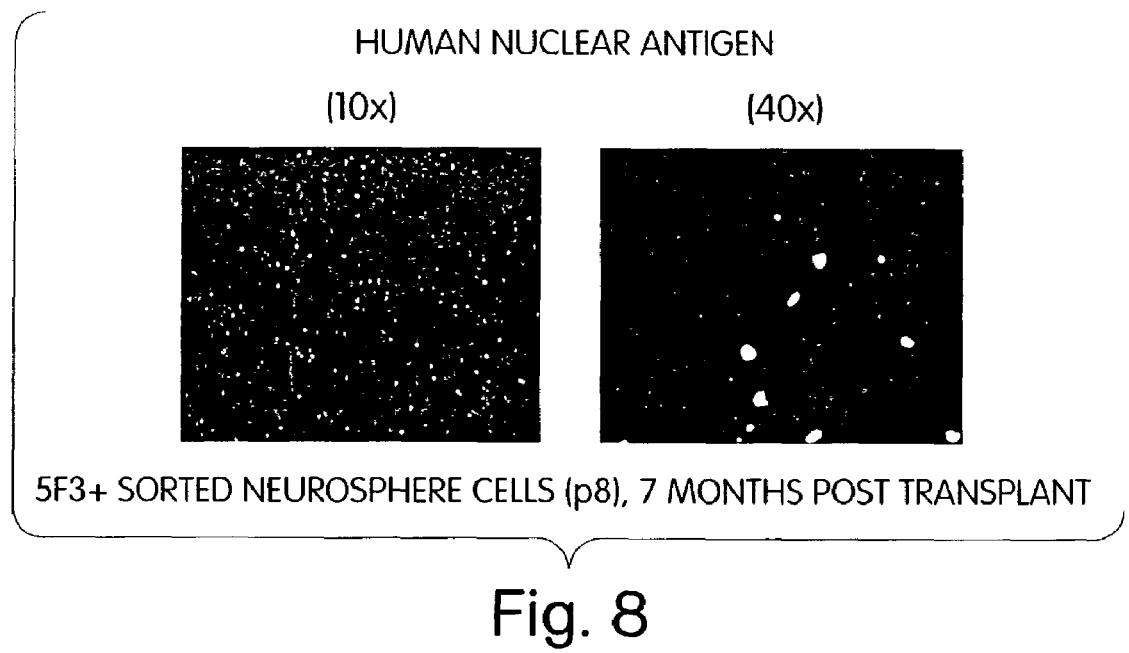
FIG. 8 is a series of photographs showing that the progeny of 5F3+ sorted cells migrate through the (RMS) into the olfactory bulb when transplanted into a rodent model.

5F3+ sorted NS-ICs (obtained as described above) were transplanted into the lateral ventricles of neonatal immunodeficient mice, using conventional techniques. Engraftment and migration of human neurosphere cells were detected between 4–8 weeks after injection using a human specific Thy-1 antibody (see FIG. 6). As shown in FIG. 7, staining with human β-tubulin (a neuron al marker) and human nuclear antigen (for localization of human cells) revealed migration of the human neurosphere cells through the rostral migratory stream (RMS). Further, as shown in FIG. 8, localization using human nuclear antigen demonstrated that human neurosphere cells had migrated through the RMS to the olfactory bulb.

EXAMPLE 9

Transplantation of CD133+ Sorted/Expanded Neurosphere Cells into Neonatal NOD-SCID Mice NOD SCID mice have provided an excellent model system for the engraftment of a number of different human cell types including the hematopoietic stem cell. Expanded CD133$^+$ sorted neurosphere cells at passages 6–10 were harvested and gently dissociated with collagenase. Neonatal mice (<24 hrs after birth) were anesthetized by placing them in ice for 5–10 minutes. Once cryo-anesthetized, the pups were placed on a stereotaxic device and injected with 1–2 ul of cells ranging from $10^5$–$10^6$ cells/injection into the lateral ventricle. The injected mice were kept 18–27 weeks prior to testing the engraftment of human cells. The AC133 antibody recognizes the CD133 antigen (see, e.g., Uchida et al., Proc. Natl. Acad. Sci. USA, 97, pp. 14720–14725 (2000)).

Generation of Human Specific Monoclonal Antibodies (MAbs) to Facilitate Analysis of the Engraftment of Various Human Neural Cell Populations Within the Context of Mouse Brains Monoclonal antibodies to human neural cells were produced using a previously described decoy immunization strategy. BALB/c mice were immunized in the left footpad with decoy human peripheral blood mononuclear cells and in the contralateral footpad with enzyme-dissociated human FBr. The right popliteal lymph node cells were fused with mouse SP2/0 cells. In order to identify human specific MAbs, the primary screen was to compare reaction of cultured mouse versus human neural cells. This screen should identify only candidate hybridomas that were human specific that could react with any epitope on a nuclear, cytoplasmic or surface molecule. These human specific MABs were tested in a final screen on sections of mouse brains that had been transplanted 18–27 weeks previously with CD133$^+$ purified and expanded neurospheres.

Immunocytochemical Analysis of Transplanted Mouse Brain

Eighteen to 27 weeks post-transplantation, the injected mice were perfused with 4% paraformaldehyde. The mouse brains were sectioned sagitally at 5–10 um thickness for fluoresce/immunohistochemical microscopic analyzer at 40 um thickness for confocal microscopy (Bio-Rad MRC1024 UV confocal scanning microscope). To detect human cells in the transplanted mouse brains, sections were stained with mouse mAbs against human nuclei (1:100; Chemicon) or human N-CAM (1:20; D. Buck), followed by goat anti-mouse IgG conjugated with Alexa 488 (1:1000, Molecular Probe) or conjugated with Cy-3 (1:500, Jackson Immunoresearch). To stain lineage-specific cell populations, sections were stained with guinea pig anti-GFAP (1:250, Advanced ImmunoChemical Inc.), rabbit anti-Ki-67 (1:1000, Novocastra), rabbit anti-tyrosine hydroxylase (1:500, PelFreeze) followed by donkey anti-guinea pig conjugated with Cy-5 (1:250, Jackson Immunoresearch) or anti-rabbit conjugated with Cy-3 (1:250; Jackson Immunoresearch). Alternatively, to detect human cells in the transplanted mouse brains, sections were stained with candidate of mouse anti human MAbs and stainings were developed immunohistochemically with peroidase using VECTORSTAIN ABC kit for mouse IgG with Nova Red substrated kit (Vector Laboratory).

Results

Potent Engraftment Ability of CD133$^+$ Sorted/Expanded Human Neurosphere Cells To evaluate in vivo engraftment migration and the differentiation capacity of sorted/expanded CD133$^+$hCNS-SC, $10^5$ or $10^6$ cells from CD133$^+$-initiated neurosphere cultures at passage 7–10 were injected into the lateral ventricles of neonatal NOD-SCID mice. Detailed analysis focused particularly on the two sites of the brain previously shown to be sites of active neurogenesis: the subventricular zone (SVZ) of the lateral ventricles and the dentate gyrus of the hippocampus. Human cells, detected with an anti-human nuclear antibody, were found throughout the brain of mice transplanted with sorted/expanded human neural cells and were abundant in the SVZ seven months after injection. Confocal microscopy indicated that most of the human cells were GFAP$^-$, but occasional human GFAP$^+$ cells were also detected. Because stem/progenitor cells in the SVZ have been shown to proliferate continuously, it was important to test whether progeny of the transplanted human CD133$^+$ sorted/expanded neurosphere cells were still proliferating in situ and co-expressed the proliferation marker Ki-67, expressed on cells in late $G_1/S/G_2/M$ phases (Schener et al., J. Cell. Biol. 123:513–22 (1993)). A cluster of human cells in the SVZ, nested in GFAP$^+$ cells, co-expressed Ki-67; like their mouse counterparts, these cells continued to proliferate 7 months post transplantation in the SVZ.

In the olfactory system of rodents, the progeny of stem/progenitor cells that have proliferated in the SVZ enter the rostral migratory stream (RMS) and migrate to the olfactory bulb (Lois et al., Science 254:1145–48 (1994); Suhanen et al., Nature (London) 383:624–27 (1996)). These endogenous rodent progenitors, the "chain of neuroblasts" in the RMS express both β-tubulin III and N-CAM (Gage et al., Isolation, Characterization and Utilization of CNS Stem Cells (Springer, Heidelberg) (1997); Fricker et al., J. Neurosci. 19:5990–6005 (1999)). Large numbers of human cells were detected in mice transplanted 7 months previously with CD133$^+$-sorted neurosphere cells, beginning in the SVZ and extending throughout the RMS. Multiple cells were identified that were double positive for both β-tubulin III and the human nuclear antigen. In addition, many of these cells in the RMS expressed the human specific marker, N-CAM (data not shown).

After migrating through the RMS, the progeny of stem/progenitor cells enter the olfactory bulb and extend toward the olfactory glomerulus to the periglomerular layers (Lois et al., Science 254:1145–48 (1994); Suhanen et al., Nature (London) 383:624–27 (1996)). The transplanted progeny of human cells distributed into the glomerular as well as the periglomerular layers. Some of these cells expressed human N-CAM, indicating that they were committed to neuron al lineages. In a few instances, human dopaminergic neurons, defined by tyrosine hydroxylase expression, were observed.

Another critical site where neurogenesis takes place in adult life is the dentate gyrus of the hippocampus (Gage et al., Isolation, Characterization, and Utilization of CNS Stem Cells (Springer, Heidelberg) (1997)). We found numerous human cells in the dentate gyrus of the hippocampus. Some of the human cells in the subgranular cell zone co-expressed Ki-67, indicating that they were still able to proliferate 7 months post-transplantation. Distinct β-tubulin III$^+$ human cells were also detected that had long axonal processes extending towards the hilus of the hippocampus as expected for developing granular neurons. These results indicate that not only do these sorted/expanded hCNS-SC engraft, migrate, continue to proliferate, and differentiate, but also their behavior and cell fate are regulated by host cues in a site-specific manner. In no case did the injected cells form tumors even 1 year after transplant into immunodeficient SCID mice.

Use of the Newly Generated Human Specific MAbs to Detect Engrafted Human Cells Within a Mouse Brain The MAb SC112 recognizes an antigen on cell surface of human cells and the MAb 6C3, is specific for human nuclei were particularly useful for assessing the extent of engraftment of human cells following transplantation of human CNS-SC into the lateral ventricle of a neonatal NOD-SCID mouse. These MAbs were used in immunohistochemical analysis on sections of transplanted mouse brain. Two areas of particular focus were the subventricular zones and the hippocampus, sites of active neurogenesis in the rodent brain. Two areas of the brain where active neurogenesis is known to occur are the dentate gyrus of the hippocampus and the subventricular zone (SVZ) of the olfactory system. A comparison of staining of the hippocampal area using a control or human specific MAb to a cell surface marker indicates the extent of human cells engrafted in this area and shows portions of axons and dendrites. Prominently seen is a neuron al cell body with extensive dendrite outgrowth in the dentate gyrus of the hippocampus with typical granular neuron in morphology. Using a human specific MAb to a nuclear antigen, large numbers of human cells can be detected in the subventricular zone (SVZ) and the rostral migratory stream (RMS). A section of the hippocampal area from another mouse with higher magnifications of morphologically distinct types of neurons within this region can also be seen. The SC112 recognizing a surface marker allowed us to easily assess the extent of human cell engraftment throughout the mouse brain. Following transplant into the lateral ventricle, human cells were detected in many mouse grafts in the non-neurogenic sites in the adult mouse brains, including cerebral cortex, striatum, mid-brain and even in the cerebellum. It appears that neonatal mouse brain has more plasticity as a host microenvironments than adult brain; therefore, engrafted human cells migrate and differentiate in wide variety of regions of the brain. As discussed briefly, the generation in vitro of human oligodendrocytes was not consistent or of significant numbers as seen by Armstrong & Svendsen. In examination of the mice brain transplanted with human CNS-SC, a significant degree of human cell engraftment in the fimbria area of the hippocampus was noted. This area is populated predominantly by oligodendrocytes. It is interesting to note that the human cells engrafted in this area are negative for the astrocytic marker GFAP and exhibit oligodendrocyte morphology. Experiments to demonstrate the formation of human oligodendrocytes in the fimbria of the hippocampus of the brain are in progress as well as further analyses of these newly generated MAbs. These human specific MAbs are believed to provide extremely valuable reagents to look for specific differences in engraftment of various subsets of human brain within the context of this mouse transplant model. Accordingly, this invention contemplates a non-human mammal engrafted with the human neural stem cells as described above. Preferably, the non-human mammal may be a rodent, most preferably a mouse. In addition the engrafted non-human mammal may be useful for drug screening and drug discovery, using well known methodologies.

EXAMPLE 10

Isolation of Human Neural Stem Cells from Fetal Brain

Neurogenesis and gliogenesis proceed from clonogeneic neural stem cells with self-renewal and multilineage differentiation properties. Human central nervous system stem cells (CNS-SC) have been directly isolated from fetal brain by flow cytometry based on the cell surface markers, including CD133$^+$. 5E12$^+$. CD34$^-$, CD45$^-$ and CD24$^{-/lo}$. CD133$^+$ CD about 1–5% of enzymatically processed fetal brain cells (16–21 gestational weeks). These non-genetically modified sorted CD133$^+$ cells continue to expand exponentially and maintain their multi-differentiation capacity for over 20 passages, including to tyrosine hydroxylase$^+$ dopaminergic neurons. Single-sorted CD133$^+$ cells initiated neurosphere cultures and the progeny of these cells could differentiated into both neurons and glia. Single cells re-isolated from sorted/expanded CD133$^+$ cells also re-initiated neurosphere cultures, demonstrating the self-renewal potential of this highly enriched stem cell population. In contrast, CD133$^-$ CD34$^-$CD45$^-$ sorted cells, which represent 95% of fetal brain cells, fail to initiate neurosphere cultures.

When these sorted/expanded CD133$^+$ neurosphere cells were transplanted into immunodeficient NOD-SCID mice, some of the grafted human cells continued to proliferate in the neurogenic sites, the subventricular zone of the lateral ventricle and the dentate gyrus of the hippocampus. In long-term engraftment (>6 months), the progeny of the human cells migrate and differentiate into neurons in the olfactory bulb, hippocampous and, in some cases, in the cerebral cortex with extensive dendrite extension. Human-derived oligodendrocytes are detected in the fimbria of the hippocampus and the corpus callosum. These human CNS-SC from fetal brain can expand in vitro and give widespread long-term (life-long) engraftment with self-renewal, migration and multilineage differentiation in the host brains under site specific regulated fashion.

EXAMPLE 11

Reisolation of Continuously Regenerating Human Neural Stem/Progenitor AC133+ Cells from Transplanted Mouse Brain Neurogenesis in adult brain involves replenishment of mature neural and glia lineages through self-renewal and differentiation of neural stem/progenitor cells. Recently, the isolation of human CNS stem cells based on cell surface markers, a clonal in vitro assay and in vivo long-term engraftment and site specific differentiation have been reported. $5F3^+(AC133)^+8G1^{-/lo}$ (hCD24) cells were enriched for neurosphere initiating cell activity while the $AC133^+hCD24^{hi}$ cells appear less primitive. $AC133^+$ $hCD24^{-/lo}$ were also isolated from adult hippocampus.

To evaluate whether progeny of transplanted human neural cells continue to self-renew, NOD SCID mice transplanted 1–12 months prior were analyzed. Some human cells in the neurogenic areas, the subventricular zone and the subgranular layer of the dentate gyrus of the hippocampus co-expressed the proliferation marker, Ki-67. To demonstrate their self-renewal potential, human neural cells from transplanted mouse brain were reisolated by immunomagnetic selection for human specific N-CAM and Thy1. Some of the positive selected cells expressed human specific antigens including AC133 or hCD24.

One month after transplantation some $AC133^+hCD24^{-/lo}$ were detected but the majority were $AC133^-hCD24^{hi}$ cells. Interestingly, the sorted $AC133^+hCD24^{-/lo}$ cells human cells from 1-year post transplanted mouse brain re-initiate neurosphere cultures. These studies suggest that the progeny of transplanted human CNS-SC continue to generate more $AC133^+$ cells as well as give rise to $AC133–hCD24^{hi}$ progenitors.

The foregoing description has been presented only for the purposes of illustration and is not intended to limit the invention to the precise form disclosed, but by the claims appended hereto.

We claim:

1. A method of producing a population enriched for human central nervous system stem cells (CNS-SC), which can initiate neurospheres (NS-IC), comprising:
   a) contacting neural or neural derived cells with monoclonal antibody 8G1;
   b) selecting said neural or neural-derived cells that bind to monoclonal antibody 8G1; and
   c) removing said bound cells wherein the remaining cells in the population are enriched for human CNS-SC,
the method further comprising the steps of further enriching a population for CNS-SC by
   d) contacting the remaining cells with a second monoclonal antibody selected from the group consisting of AC133 and 5E12, and
   e) selecting those cells that bind to said second monoclonal antibody to produce a population enriched for CNS-SC.

2. The method of claim 1, wherein the monoclonal antibodies are fluorochrome conjugated.

3. The method of claim 1, wherein the monoclonal antibodies are conjugated to magnetic particles.

4. The method of claim 1, wherein the selecting is by flow cytometry.

5. The method of claim 1, wherein the selecting is by fluorescence activated cell sorting or high gradient magnetic selection.

6. The method of claim 1, wherein the selecting is by attachment to and disattachment from the solid phase.

7. The method of claim 1, wherein the population containing neural or neural-derived cells is obtained from a neurosphere culture or an adherent culture.

8. The method of claim 1, wherein the population containing neural or neural-derived cells is obtained from neural tissue.

9. A method for producing a population enriched for human central nervous system stem cells (CNS-SC) which can initiate neurospheres (NS-IC) comprising eliminating from a population of neural or neural-derived cells those cells that are $CD24^{+,}$ the method further comprising the step of further enriching the population for CNS-SC by selecting from the remaining population of neural or neural-derived cells for cells that bind to monoclonal antibody AC133.

10. A method for producing a population enriched for human central nervous system stem cells (CNS-SC) which can initiate neurospheres (NS-IC) comprising eliminating from a population of neural or neural-derived cells those cells that are $CD24^{+,}$ the method further comprising the step of further enriching the population for CNS-SC by selecting from the remaining population of neural or neural-derived cells for cells that bind to monoclonal antibody 5E12.

11. The method of claim 9, further comprising the step of further enriching the population by selecting for cells that bind to monoclonal antibody 5E12.

12. The method of claim 10, further comprising the step of further enriching the population by selecting for cells that bind to monoclonal antibody AC133.

13. A method for enriching from a population of neural cells for the populations of neurosphere initiating stem cell (NS-IC) fraction, comprising selecting from the neural cells for cells that bind to monoclonal antibody 8G1 and removing said cells from said population, wherein the remaining cells are enriched in the fraction of NS-IC as compared with the population of neural cells, the method further comprising the step of further enriching for the fraction of NS-IC by selecting from the remaining cells for cells that bind to monoclonal antibody AC133 or to monoclonal antibody 5E12.

14. A method for isolating a neurosphere initiating stem cell (NS-IC), comprising:
   a) selecting from a population of neural or neural-derived cells for cells that are $CD24^+$;
   b) eliminating said $CD24^+$cells from the population;
   c) selecting from the remaining population for at least one cell that binds to monoclonal antibody AC133 or to monoclonal antibody 5E12;
   d) introducing at least one selected cell to a serum-free culture medium containing one or more growth factors selected from the group consisting of LIF, EGF, bFGF, and combinations thereof; and
   e) proliferating at least one selected cell in the culture medium.

15. A method for producing a population enriched for human central nervous system stem cells (CNS-SC) which can initiate neurospheres (NS-IC) comprising selecting from a population of neural or neural-derived cells for cells that bind to monoclonal antibody AC133.

16. A method for producing a population enriched for human central nervous system stem cells (CNS-SC) which can initiate neurospheres (NS-IC) comprising selecting from neural or neural-derived cells for cells that bind to monoclonal antibody AC133 or to monoclonal antibody 5E12, to produce a population enriched for CNS-SC, wherein the selecting is by attachment to and disattachment from solid phase.

17. A method for the enrichment of human central nervous system neural stem cells (CNS-SC) which can initiate neurospheres (NS-IC), said method comprising:
a) combining a population of neural or neural-derived cells with an antibody that binds to the CD24 antigen; and
b) selecting for those cells that do not bind to the CD24 antigen, wherein the selected cells are enriched for CNS-SC, the method further comprising the step of further enriching the population for CNS-SC by selecting from the remaining population of neural or neural-derived cells for cells that bind to monoclonal antibody AC133 or to monoclonal antibody 5E12.

18. The method according to claim 17, wherein at least one of said antibodies is fluorochrome conjugated.

19. The method according to claim 18, wherein said selecting with said fluorochrome conjugated antibodies is by flow cytometry.

20. The method according to claim 17, wherein at least of one of said antibodies is conjugated to magnetic particles.

21. The method of claim 20, wherein said selecting with said magnetic particle conjugated antibodies is by high gradient magnetic selection.

22. The method of claim 9, wherein said elimination is accomplished by contacting the population of cells with monoclonal antibody 8G1 and removing those cells that bind to monoclonal antibody 8G1.

23. The method of claim 10, wherein said elimination is accomplished by contacting the population of cells with monoclonal antibody 8G1 and removing those cells that bind to monoclonal antibody 8G1.

* * * * *